(12) United States Patent
Takeshima

(10) Patent No.: US 11,493,585 B2
(45) Date of Patent: Nov. 8, 2022

(54) MEDICAL INFORMATION PROCESSING APPARATUS AND MEDICAL INFORMATION PROCESSING METHOD

(71) Applicant: Canon Medical Systems Corporation, Otawara (JP)

(72) Inventor: Hidenori Takeshima, Kawasaki (JP)

(73) Assignee: Canon Medical Systems Corporation, Otawara (JP)

( * ) Notice: Subject to any disclaimer, the term of this patent is extended or adjusted under 35 U.S.C. 154(b) by 805 days.

(21) Appl. No.: 16/452,818

(22) Filed: Jun. 26, 2019

(65) Prior Publication Data

US 2020/0003858 A1    Jan. 2, 2020

(30) Foreign Application Priority Data

Jun. 29, 2018 (JP) .............................. JP2018-124088
Jun. 24, 2019 (JP) .............................. JP2019-116625

(51) Int. Cl.
*G06F 15/18* (2006.01)
*G01R 33/56* (2006.01)
(Continued)

(52) U.S. Cl.
CPC .......... *G01R 33/5608* (2013.01); *A61B 5/055* (2013.01); *A61B 5/7203* (2013.01); *A61B 5/7257* (2013.01); *A61B 5/7267* (2013.01); *G06K 9/6298* (2013.01); *G06N 20/00* (2019.01); *G06T 11/003* (2013.01); *G16H 30/40* (2018.01)

(58) Field of Classification Search
CPC .............. G01R 33/5608; G01R 33/482; G01R 33/4824; G01R 33/5602; G01R 33/5611; A61B 5/055; A61B 5/7203; A61B 5/7257; A61B 5/7267; A61B 2576/00; G06K 9/6298; G06K 9/6271; G06N 20/00; G06N 3/0454; G06N 3/084; G06T 11/003;
(Continued)

(56) References Cited

U.S. PATENT DOCUMENTS 9,799,120 B1 * 10/2017 Fenchel .................... G06T 7/11
11,143,730 B2 * 10/2021 Wang ................. G01R 33/5608
(Continued)

FOREIGN PATENT DOCUMENTS

CA    2732171 A1 *  3/2010 ............ G16H 30/40
JP    2019-159914 A    9/2019
(Continued)

OTHER PUBLICATIONS

Schlemper, J, et al., "A Deep Cascade of Convolutional Neural Networks for MR Image Reconstruction", Mar. 2017, 12 pages.
(Continued)

*Primary Examiner* — Mahendra R Patel
(74) *Attorney, Agent, or Firm* — Oblon, McClelland, Maier & Neustadt, L.L.P.

(57) ABSTRACT

According to one embodiment, a medical information processing apparatus has processing circuitry. The processing circuitry acquires medical data on a subject, acquires numerical data obtained by digitizing an acquisition condition of the medical data, and applies a machine learning model to input data including the numerical data and the medical data, thereby generating output data based on the medical data.

20 Claims, 15 Drawing Sheets

(51) Int. Cl.
  *G16H 30/40*   (2018.01)
  *G06N 20/00*   (2019.01)
  *A61B 5/00*    (2006.01)
  *A61B 5/055*   (2006.01)
  *G06K 9/62*    (2022.01)
  *G06T 11/00*   (2006.01)

(58) Field of Classification Search
  CPC ........ G16H 30/40; G16H 40/63; G16H 50/20; G06V 2201/03; G06V 10/82
  USPC .......................................................... 706/12
  See application file for complete search history.

(56) References Cited

U.S. PATENT DOCUMENTS

| | | | | |
|---|---|---|---|---|
| 2005/0027995 | A1* | 2/2005 | Menschik | G16H 40/67 713/193 |
| 2012/0155730 | A1* | 6/2012 | Metaxas | G01R 33/5608 382/131 |
| 2013/0024382 | A1* | 1/2013 | Dala | H04L 63/0464 705/51 |
| 2016/0071291 | A1* | 3/2016 | Samsonov | A61B 6/032 600/410 |
| 2017/0007148 | A1* | 1/2017 | Kaditz | A61B 5/055 |
| 2018/0144466 | A1* | 5/2018 | Hsieh | G06T 7/0012 |

FOREIGN PATENT DOCUMENTS

| | | | |
|---|---|---|---|
| JP | 2019159914 A | * 9/2019 | |
| WO | WO-03085574 A1 | * 10/2003 | ........... G06F 19/323 |
| WO | WO-2018187005 A1 | * 10/2018 | ........... G01R 33/482 |

OTHER PUBLICATIONS

Zhu, B, et al., "Image reconstruction by domain-transform manifold learning", Nature, vol. 555, Mar. 22, 2018, pp. 487-492.

Feng, L, et al., "XD-GRASP: Golden Angle Radial MRI with Reconstruction of Extra Motion-State Dimensions Using Compressed Sensing", Magnetic Resonance in Medicine, vol. 75, 2016, pp. 775-788.

Zhu, B, et al., "Deep Learning MR reconstruction with Automated Transform by Manifold Approximation (AUTOMAP) in real-world acquisitions with imperfect training: simulation and in-vivo experiments," ISMRM Workshop on Machine Learning, Mar. 2018, 1 page.

* cited by examiner

Set of acquisition line candidates
having finite number of elements
(Conceptual Drawing)

Select 1, 4, 7

Digitizing

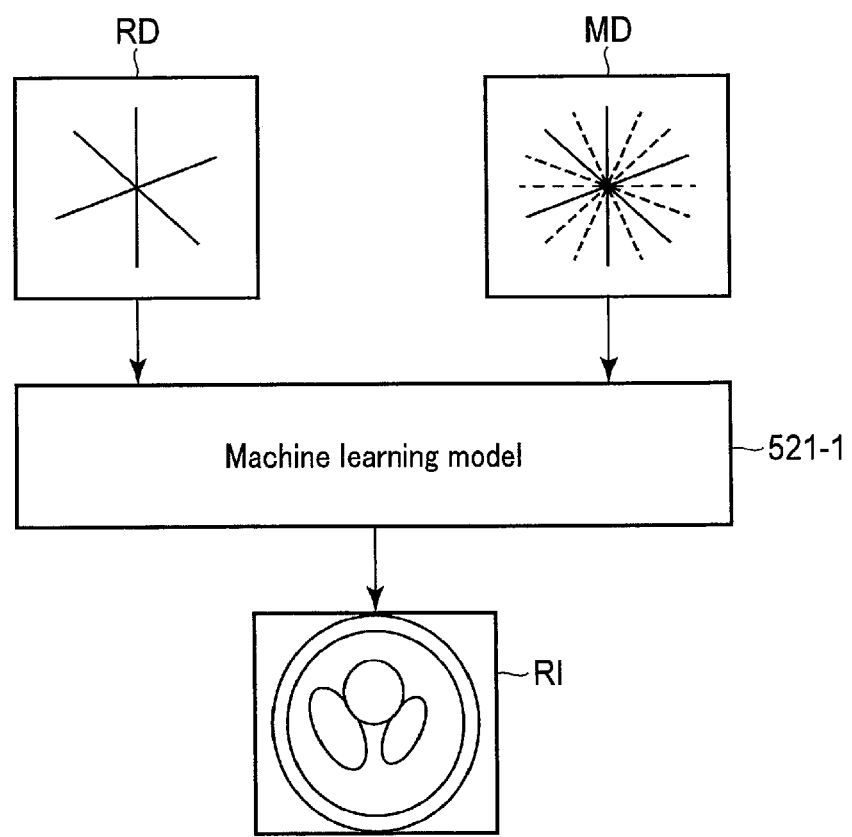
F I G. 4

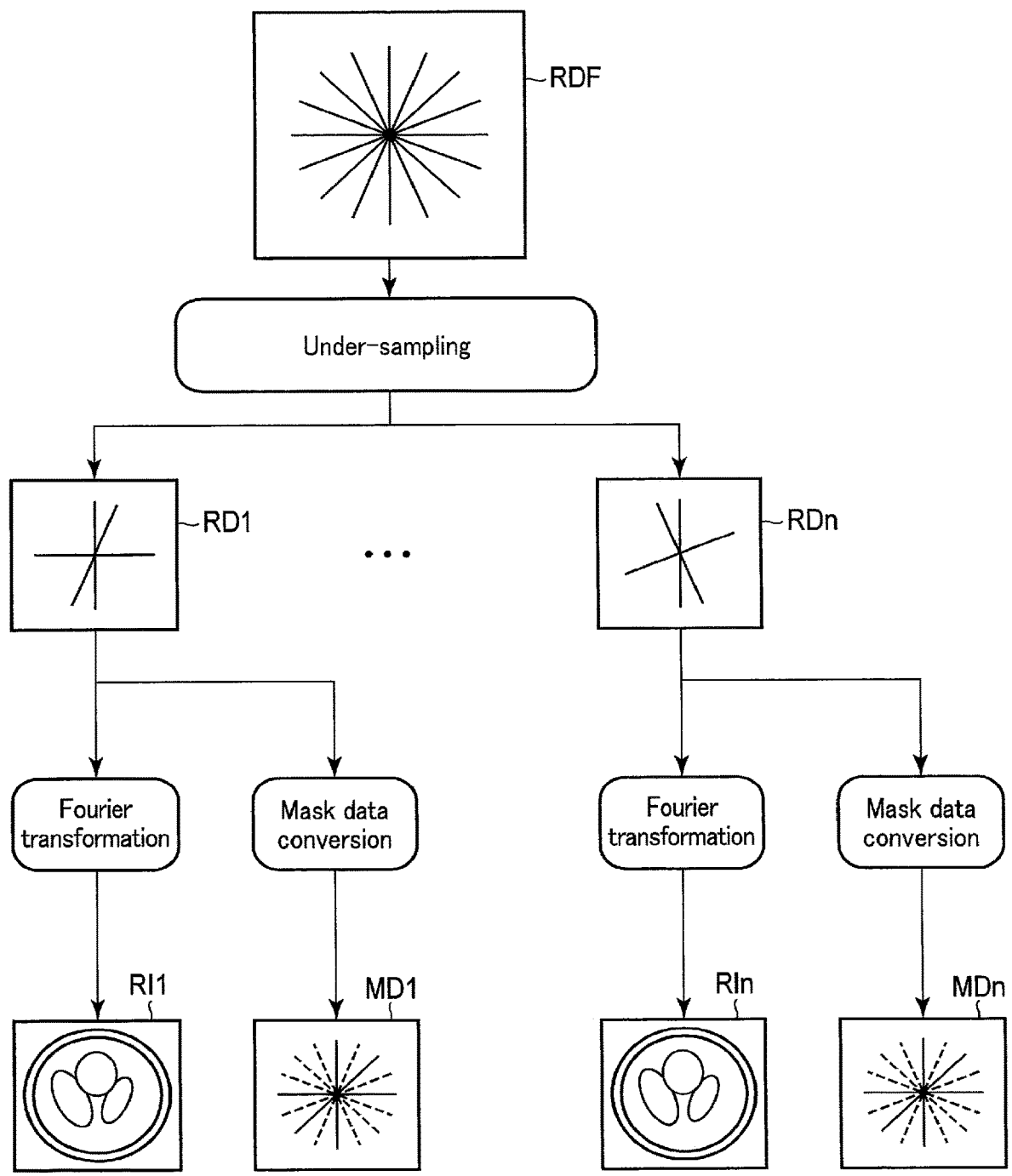
F I G. 8

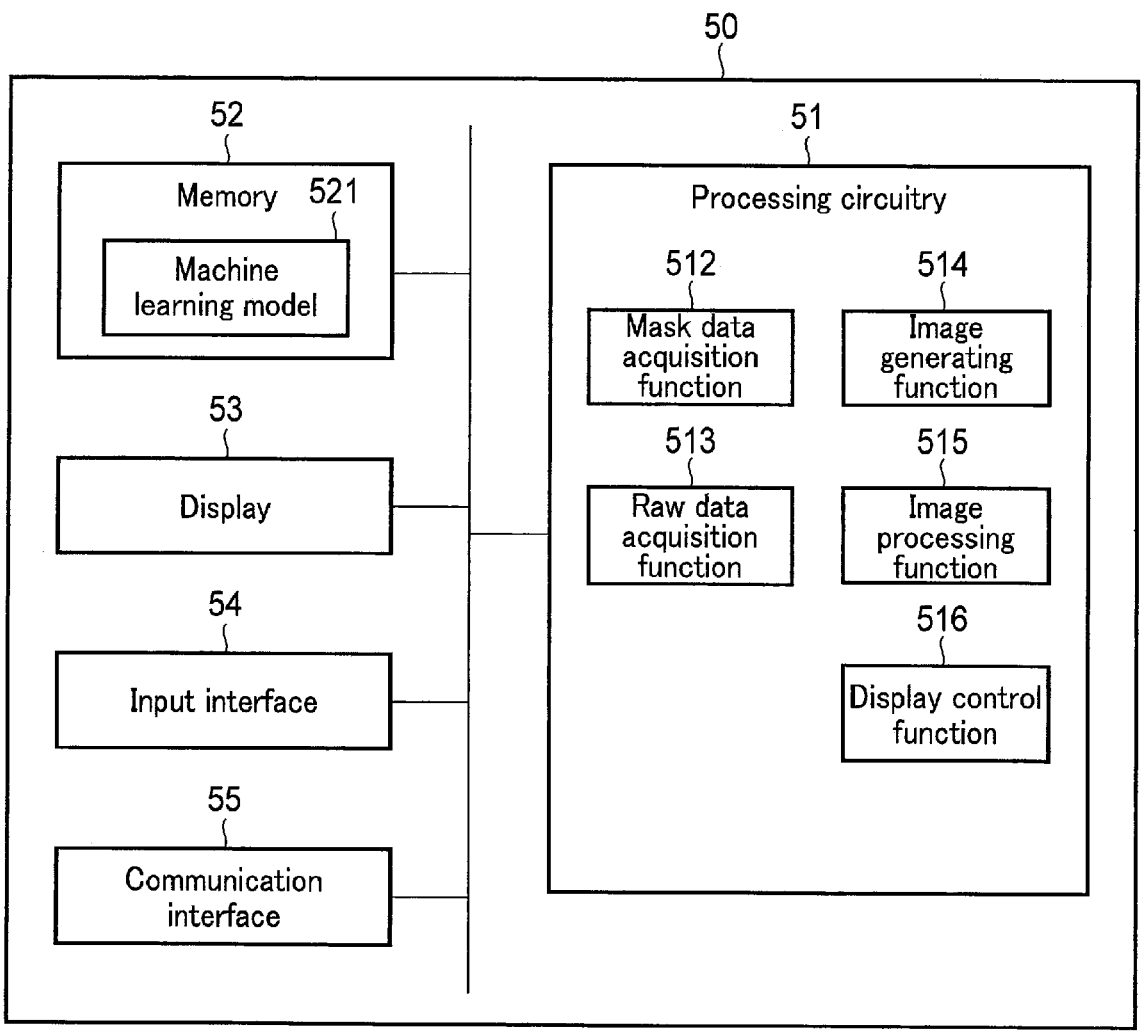
F I G. 9
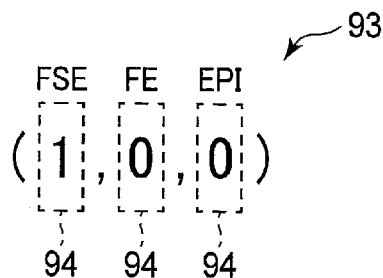
F I G. 10

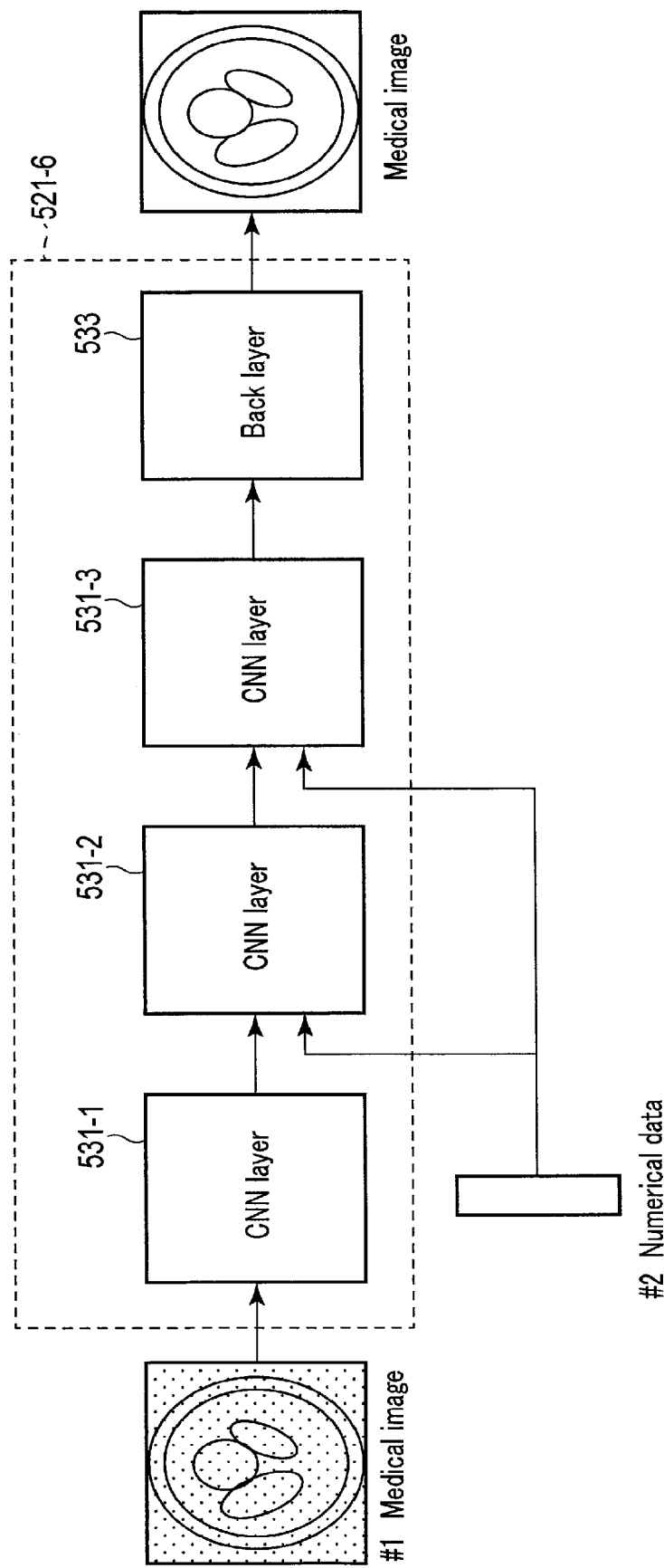
F I G. 17

MEDICAL INFORMATION PROCESSING APPARATUS AND MEDICAL INFORMATION PROCESSING METHOD

CROSS-REFERENCE TO RELATED APPLICATIONS

This application is based upon and claims the benefit of priority from the Japanese Patent Application No. 2018-124088, filed Jun. 29, 2018 and the Japanese Patent Application No. 2019-116625, filed Jun. 24, 2019 the entire contents of all of which are incorporated herein by reference.

FIELD

Embodiments described herein relate generally to a medical information processing apparatus and a medical information processing method.

BACKGROUND

In machine learning using medical data such as medical image data and its raw data, there is a method to apply a deep neural network (DNN) learned from a number of training data in order to restore original data from partly deficient medical data. For example, in magnetic resonance imaging (MRI), there is a method of applying DNN to k-space data undersampled by cartesian acquisition to generate the k-space data in which a deficient part is restored, and obtaining a reconstructed image based on the k-space data after restoration. There is also a method of applying DNN to undersampled k-space data to directly obtain a restored image.

BRIEF DESCRIPTION OF THE DRAWING

FIG. 4 is a drawing schematically showing a flow of the first DNN reconstruction according to the present embodiment.

FIG. 8 is a drawing schematically showing processing performed by a training sample generating function of FIG. 7.

FIG. 9 is a view showing another configuration of the medical information processing apparatus according to the present embodiment.

FIG. 10 is a drawing schematically showing numerical data according to the present embodiment.

FIG. 17 is a drawing schematically showing input and output of a machine learning model having a plurality of CNNs.

DETAILED DESCRIPTION

In general, according to one embodiment, a medical information processing apparatus has processing circuitry. The processing circuitry acquires medical data on a subject, acquires numerical data obtained by digitizing an acquisition condition of the medical data, and applies a machine learning model to input data including the numerical data and the medical data, thereby generating output data based on the medical data.

Hereinafter, a medical information processing apparatus and a medical information processing method according to the present embodiment will be described with reference to the drawings.

The medical information processing apparatus according to the present embodiment is an apparatus in which a processing circuitry that processes medical information is mounted. The medical information processing apparatus according to the present embodiment is realized, for example, by a computer mounted on a medical image diagnostic apparatus. The medical image diagnostic apparatus according to the present embodiment may be a single modality apparatus such as a magnetic resonance imaging apparatus (MRI apparatus), an X-ray computed tomography apparatus (CT apparatus), an X-ray diagnostic apparatus, a PET (Positron Emission Tomography) apparatus, a single photon emission CT apparatus (SPECT apparatus), and an ultrasonic diagnostic apparatus, and also may be a combined modality apparatus such as a PET/CT apparatus, a SPECT/CT apparatus, a PET/MRI apparatus, and a SPECT/MRI apparatus. As other examples, the medical information processing apparatus according to the present embodiment may be a computer communicably connected to the medical image diagnostic apparatus via a cable, a network, or the like, or may be a computer independent of the medical image diagnostic apparatus. Hereinafter, the medical information processing apparatus according to the present embodiment is assumed to be mounted on the magnetic resonance imaging apparatus.

Figure 1:
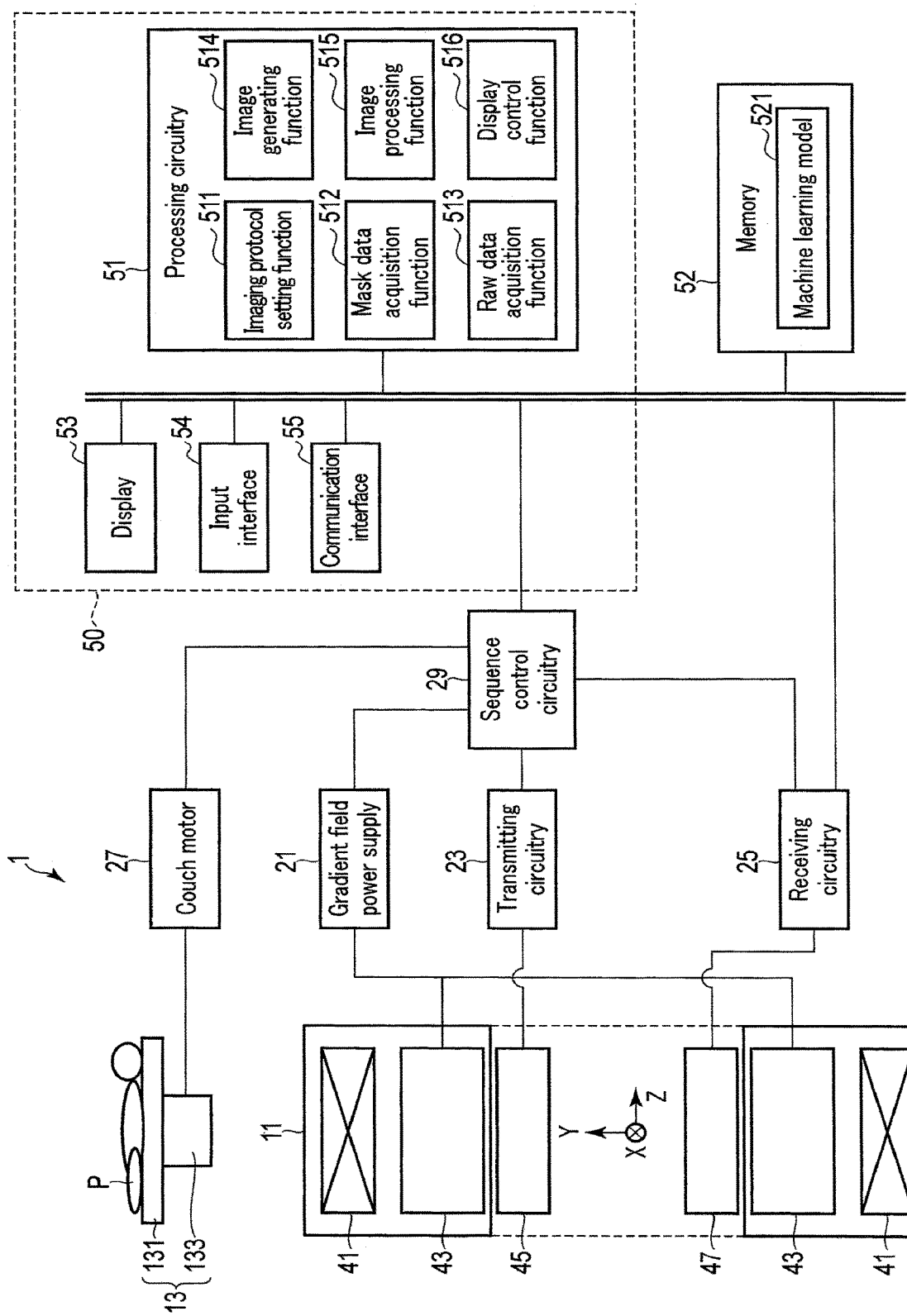
FIG. 1 is a view showing a configuration of a magnetic resonance imaging apparatus on which a medical information processing apparatus according to the present embodiment is mounted.

FIG. 1 is a view showing a configuration of a magnetic resonance imaging apparatus 1 on which a medical information processing apparatus 50 according to the present embodiment is mounted; As shown in FIG. 1, the magnetic resonance imaging apparatus 1 includes a gantry 11, a couch 13, a gradient field power supply 21, a transmitting circuitry 23, a receiving circuitry 25, a couch motor 27, a sequence control circuitry 29, and the medical information processing apparatus 50.

The gantry 11 has a static field magnet 41 and a gradient field coil 43. The static field magnet 41 and the gradient field coil 43 are accommodated in a housing of the gantry 11. The housing of the gantry 11 is formed with a bore having a hollow shape. A transmitting coil 45 and a receiving coil 47 are disposed in the bore of the gantry 11.

The static field magnet 41 has a hollow substantially cylindrical shape and generates a static magnetic field inside a substantially cylindrical interior. Examples of the static field magnet 41 used include a permanent magnet, a superconducting magnet or a normal conducting magnet. Here, a central axis of the static field magnet 41 is defined as a Z axis, an axis perpendicular to the Z axis is defined as a Y axis, and an axis perpendicular to the Z axis is defined as an X axis. The X axis, the Y axis and the Z axis constitute an orthogonal three-dimensional coordinate system.

The gradient field coil 43 is a coil unit attached to the inside of the static field magnet 41 and formed in a hollow substantially cylindrical shape. The gradient field gradient field coil 43 receives supply of a current from the gradient field power supply 21 to generate a gradient field. More specifically, the gradient field coil 43 has three coils corresponding to the X axis, the Y axis, and the Z axis orthogonal to each other. The three coils form a gradient field in which the magnetic field strength changes along the X axis, the Y axis, and the Z axis respectively. The gradient fields respectively along the X axis, the Y axis, and the Z axis are combined to form slice selection gradient fields Gs, phase encoding gradient fields Gp, and frequency encoding gradient fields Gr that are orthogonal to each other in arbitrary directions. The slice selection gradient fields Gs are used to determine the imaging cross section arbitrarily. The phase encoding gradient fields Gp are used to change the phase of the MR signal according to the spatial position. The frequency encoding gradient fields Gr are used to change the frequency of the MR signal according to the spatial position. It should be noted that in the following description, it is assumed that the direction of gradient of the slice selection gradient fields Gs corresponds to the Z axis, the direction of gradient of the phase encoding gradient fields Gp corresponds to the Y axis, and the direction of gradient of the frequency encoding gradient fields Gr corresponds to the X axis.

The gradient field power supply 21 supplies a current to the gradient field coil 43 in accordance with a sequence control signal from the sequence control circuitry 29. The gradient field power supply 21 supplies a current to the gradient field coil 43 and cause the gradient field coil 43 to generate a gradient field along each of the X axis, Y axis, and Z axis. The gradient field is superimposed on the static magnetic field formed by the static field magnet 41 and applied to a subject P.

The transmitting coil 45 is disposed, for example, inside the gradient field coil 43, and receives supply of a current from the transmitting circuitry 23 to generate a high frequency magnetic field pulse (hereinafter referred to as an RF magnetic field pulse).

The transmitting circuitry 23 supplies a current to the transmitting coil 45 in order to apply an RF magnetic field pulse for exciting a target proton in the subject P to the subject P via the transmitting coil 45. The RF magnetic field pulse oscillates at a resonance frequency specific to the target proton to excite the target proton. A magnetic resonance signal (hereinafter referred to as an MR signal) is generated from the excited target proton and detected by the receiving coil 47. The transmitting coil 45 is, for example, a whole-body coil (WB coil). The whole-body coil may be used as a transmitting and receiving coil.

The receiving coil 47 receives the MR signal emitted from the target proton present in the subject P under an action of the RF magnetic field pulse. The receiving coil 47 has a plurality of receiving coil elements capable of receiving the MR signal. The MR signal received is supplied to the receiving circuitry 25 via wire or wireless. Although not shown in FIG. 1, the receiving coil 47 has a plurality of receiving channels implemented in parallel. The receiving channels each include receiving coil elements that receives the MR signal, an amplifier that amplifies the MR signal, and the like. The MR signal is output for each receiving channel. The total number of the receiving channels and the total number of the receiving coil elements may be the same, or the total number of the receiving channels may be larger or smaller than the total number of the receiving coil elements.

The receiving circuitry 25 receives the MR signal generated from the excited target proton via the receiving coil 47. The receiving circuitry 25 processes the MR signal received to generate a digital MR signal. The digital MR signal can be expressed in k-space defined by a spatial frequency. Therefore, hereinafter, the digital MR signal is referred to as k-space data. The k-space data is a type of raw data to be provided for image reconstruction. The k-space data is supplied to the medical information processing apparatus 50 via wire or wireless.

It should be noted that the transmitting coil 45 and the receiving coil 47 described above are merely examples. Instead of the transmitting coil 45 and the receiving coil 47, a transmitting and receiving coil having a transmitting function and a receiving function may be used. Also, the transmitting coil 45, the receiving coil 47, and the transmitting and receiving coil may be combined.

The couch 13 is installed adjacent to the gantry 11. The couch 13 has a table top 131 and a base 133. The subject P is placed on the table top 131. The base 133 slidably supports the table top 131 respectively along the X axis, the Y axis, and the Z axis. The couch motor 27 is accommodated in the base 133. The couch motor 27 moves the table top 131 under the control of the sequence control circuitry 29. The couch motor 27 may include any motor such as a servo motor or a stepping motor for example.

The sequence control circuitry 29 has a processor of a Central Processing Unit (CPU) or a micro processing unit (MPU) and a memory such as a read only memory (ROM) or a random access memory (RAM) as hardware resources. The sequence control circuitry 29 synchronously controls the gradient field power supply 21, the transmitting circuitry 23, and the receiving circuitry 25 based on the imaging protocol determined by an imaging protocol setting function 511 of the processing circuitry 51, executes a pulse sequence corresponding to the imaging protocol to MR imaging the subject P, and acquires the k-space data on the subject P.

As shown in FIG. 1, the medical information processing apparatus 50 is a computer apparatus having a processing circuitry 51, a memory 52, a display 53, an input interface 54, and a communication interface 55.

The processing circuitry 51 includes, as hardware resources, a processor such as a CPU, a Graphics Processing Unit (GPU), and a MPU, and a memory such as a ROM and a RAM. The processing circuitry 51 functions as the center of the magnetic resonance imaging apparatus 1. For example, the processing circuitry 51 has the imaging protocol setting function 511, a mask data acquisition function 512, a raw data acquisition function 513, an image generating function 514, an image processing function 515, and a display control function 516 by executing various programs.

In the imaging protocol setting function 511, the processing circuitry 51 sets an imaging protocol relating to MR imaging of a target by user instruction via the input interface 54 or automatically. The imaging protocol is a set of various imaging parameters related to one MR imaging. Examples of applicable imaging parameters according to the present embodiment include various imaging parameters set directly or indirectly for performing MR imaging such as imaging time, type of k-space filling method, type of pulse sequence, TR, TE and the like.

In the mask data acquisition function 512, the processing circuitry 51 acquires mask data regarding MR imaging of a target. The mask data is data in which numerical values corresponding to the number of times of acquisition and/or the direction of acquisition in target imaging are assigned to a plurality of data acquisition trajectory candidates having a finite number of elements. The data acquisition trajectory refers to an acquisition trajectory of raw data on k-space and relates to the type of k-space filling method. For example, if the k-space filling method is a radial method, the data acquisition trajectory is a general line (spoke) passing through the center of k-space. When the k-space filling method is a spiral method or a variable density spiral method, the data acquisition trajectory is a spiral-shaped curve from the center to the outer periphery of k-space. Acquisition of mask data includes processing such as generation of mask data by the processing circuitry 51, selection of any one mask data from among a plurality of mask data, reception, transfer, transmission, and the like of mask data from another apparatus.

The raw data acquisition function 513 acquires k-space data. Acquisition of k-space data includes acquisition of k-space data by MR imaging performed under the control of the processing circuitry 51, selection of any one of k-space data from among the plurality of k-space data, reception transfer or transmission of k-space data from other apparatuses.

In the image generating function 514, the processing circuitry 51 performs reconstruction processing using the machine learning model 521 on the mask data acquired by the mask data acquisition function 512 and the k-space data acquired by the raw data acquisition function 513, and generates an MR image of the subject P. The machine learning model 521 is stored in the memory 52. The machine learning model 521 is a parameterized synthesis function defined by a combination of a plurality of adjustable functions and parameters (weighting matrices or biases). The machine learning model 521 is realized by a deep network model (DNN: Deep Neural Network) having an input layer, an intermediate layer, and an output layer. Hereinafter, the reconstruction processing using the machine learning model 521 will be referred to as DNN reconstruction.

In the image processing function 515, the processing circuitry 51 performs various image processing on the MR image. For example, the processing circuitry 51 performs image processing such as volume rendering, surface rendering, pixel value projection processing, Multi-Planer Reconstruction (MPR) processing, Curved MPR (CPR) processing, and the like.

In the display control function 516, the processing circuitry 51 displays various information on the display 53. For example, the processing circuitry 51 displays the MR image generated by the image generating function 514, the MR image generated by the image processing function 515, an imaging protocol setting screen, and the like on the display 53.

The memory 52 is a storage apparatus such as a hard disk drive (HDD), a solid state drive (SSD), an integrated circuitry storage apparatus or the like that stores various information. Further, the memory 52 may be a drive apparatus or the like that reads and writes various information from and to a portable storage medium such as a CD-ROM drive, a DVD drive, a flash memory, and the like. For example, the memory 52 stores k-space data, a control program, a machine learning model 521, and the like.

The display 53 displays various information. For example, the display 53 displays an MR image generated by the image generating function 514, an MR image generated by the image processing function 515, a setting screen of an imaging protocol, and the like. Examples of the display 53 that can be used appropriately include a CRT display, a liquid crystal display, an organic EL display, an LED display, a plasma display, or any other display known in the art.

The input interface 54 includes an input apparatus that receives various commands from the user. Examples of the input apparatus that can be used appropriately include a keyboard, a mouse, various switches, a touch screen, a touch pad, and the like. It should be noted that the input apparatus is not limited to those having physical operation parts such as the mouse and the keyboard. For example, the examples of input interface 54 also include an electrical signal processing circuitry that receives an electrical signal corresponding to an input operation from an external input apparatus provided separately from the magnetic resonance imaging apparatus 1 and outputs the electrical signal received to various circuitry.

The communication interface 55 is an interface connecting the magnetic resonance imaging apparatus 1 with a workstation, a picture archiving and communication system (PACS), a hospital information system (HIS), a radiology information system (RIS), and the like via a local area network (LAN) or the like. The network IF transmits and receives various information to and from the connected workstation, PACS, HIS and RIS.

It should be noted that the above configuration is merely an example, and the present invention is not limited thereto. For example, the sequence control circuitry 29 may be incorporated into the medical information processing apparatus 50. Also, the sequence control circuitry 29 and the processing circuitry 51 may be mounted on the same substrate. The sequence control circuitry 29, the gradient field power supply 21, the transmitting circuitry 23 and the receiving circuitry 25 may be mounted on a single control apparatus different from the medical information processing apparatus 50 or may be distributed and mounted on a plurality of apparatuses.

Hereinafter, an operation example of the magnetic resonance imaging apparatus 1 and the medical information processing apparatus 50 according to the present embodiment will be described.

Figure 2:
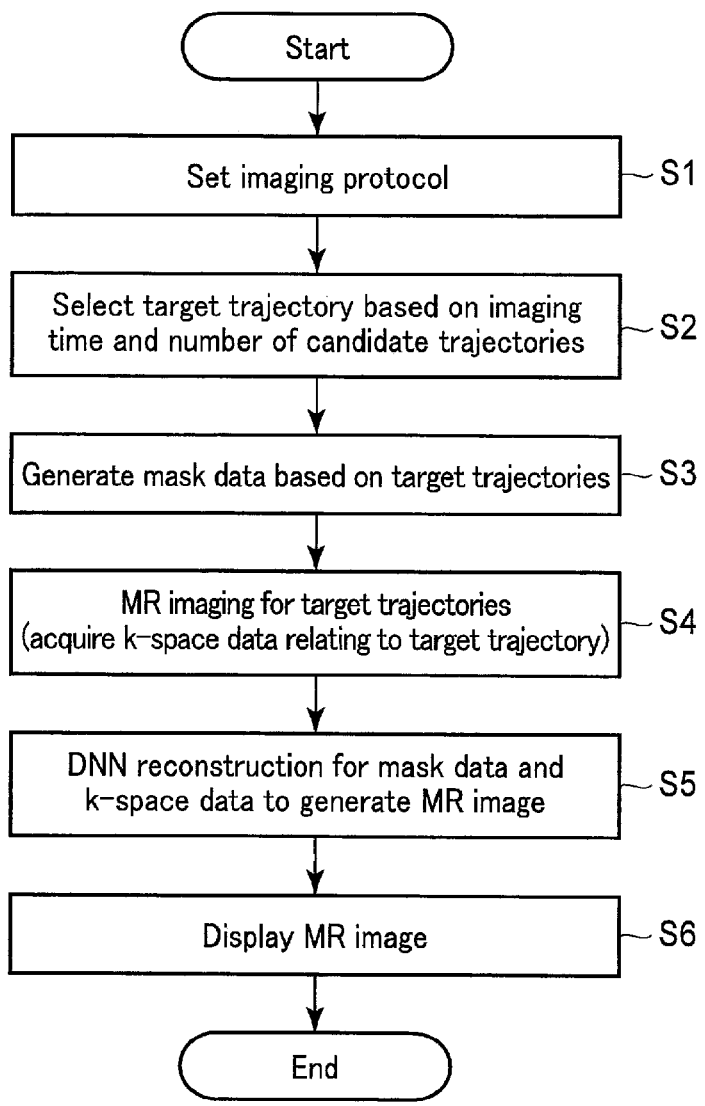
FIG. 2 is a drawing showing a typical flow of MR imaging by a processing circuitry of FIG. 1.

FIG. 2 is a drawing showing a typical flow of MR imaging by the processing circuitry 51 The process shown in FIG. 2 starts with setting of the imaging protocol of the target MR imaging.

As shown in FIG. 2, the processing circuitry 51 executes an imaging protocol setting function 511 (Step S1). In Step S1, the processing circuitry 51 sets an imaging protocol related to the subject P. As imaging parameters included in the imaging protocol, imaging time, type of k-space filling method, type of pulse sequence, TR, TE and the like are set. In the present embodiment, the type of k-space filling method may be any method such as the radial method, the spiral method, and the Cartesian method. However, in order to specifically explain the following description, it is assumed that the k-space filling method is the radial method.

When Step S1 is performed, the processing circuitry 51 executes the mask data acquisition function 512 (Steps S2 and S3). In Steps S2 and S3, the processing circuitry 51 generates mask data regarding MR imaging of a target. The mask data is data in which numerical values indicating that a plurality of candidates of the data acquisition trajectories (spokes) having a finite number of elements are to be acquired or not to be acquired in target imaging are assigned. In other words, the mask data is data indicating a trajectory to be acquired among candidate trajectories having a finite number of elements.

Figure 3:
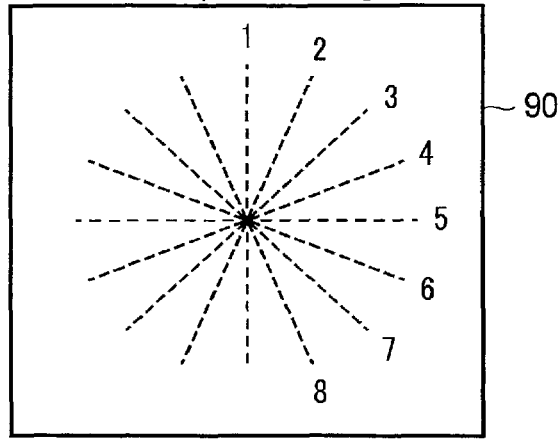
FIG. 3 is a drawing schematically showing a process of generating mask data in Steps S2 and S3 of FIG. 2.
Figure 3:
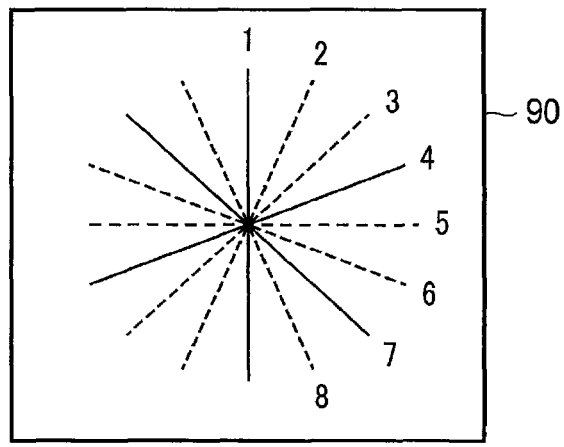
Figure 3:
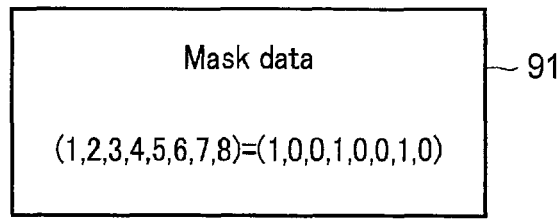

FIG. 3 is a drawing schematically showing the process of generating mask data 91 in Steps S2 and S3. As shown in FIG. 3, the data acquisition trajectory relating to the radial method passes radially at substantially the center of the k-space. As shown in the upper part of FIG. 3, in the MR imaging according to the present embodiment, data acquisition trajectory to be acquired (hereinafter, referred to as trajectories to be acquired) is selected from a set 70 of candidates of the data acquisition trajectories having a predetermined finite number of elements (hereinafter referred to as candidate trajectories). The candidate trajectories are shown by dotted lines in FIG. 3. The number of the elements and the angle of the candidate trajectories (number) are set in advance. The number of the elements of the candidate trajectories is set to a number that can ensure sufficient image quality when data acquisition is performed for all candidate trajectories having the number of the elements. The number of the elements of the candidate trajectories is preferably finite. In other words, if the number of the elements of the candidate trajectories is not an irrational number, for example, it may be a large number such as one million. It should be noted that FIG. 3 shows eight candidate trajectories for the sake of simplicity of the drawing.

The angle of the candidate trajectories according to the present embodiment is defined as a reference angle, for example, an angle from 0 degree. The angular interval of adjacent candidate trajectories is set to a predetermined angle. Specifically, it is preferable that the angular interval of adjacent candidate trajectories be set at substantially equal intervals. Thus, by limiting the number of the elements and the angle, it is possible to also limit the number of the elements and the angle of candidate trajectories of training data of machine learning.

The acquisition angle of each candidate trajectory is set to a multiple of the basic angle. In other words, assuming that the acquisition angle of the first data acquisition trajectory is 0 degrees, setting would be the acquisition angle of the second candidate trajectory=basic angle, the acquisition angle of the third candidate trajectory="basic angle×2", and the acquisition angles of the fourth candidate trajectory="basic angle×3", . . . and so forth.

The basic angle may be set to a golden angle, for example, an irrational number of approximately 111.25 degrees if the number of the elements is limited. For example, when the number of the elements is 1000, the acquisition angle of the first candidate trajectory is set to 0 degrees, the acquisition angle of the second candidate trajectory is set to the golden angle, and the acquisition angle of the third candidate trajectory is set to "the golden angle×2", the acquisition angle of the fourth candidate trajectory is set to "the golden angle×3", . . . and so forth up to the 1000th candidate trajectory.

The acquisition angle may be set to a value obtained by dividing 360 degrees by the number of the elements. For example, when the number of the elements is 1000, the basic angle may be set to 360/1000 degrees=0.36 degrees. Also, the basic angle may be set to a multiple of 360/1000 degrees. For example, if the multiple is 309, the basic angle will be set to 360/1000 degrees×309=111.24 degrees. This allows the basic angle to be substantially equal to the golden angle.

Number for identification (hereinafter referred to as a trajectory number) are assigned to the candidate trajectories. The trajectory number is used to generate mask data. The rule of trajectory number assignment may be any rule. For example, numbers may be assigned in order from candidate trajectories with small or large acquisition angles, or numbers may be assigned according to the setting order of candidate trajectories.

First, the processing circuitry 51 selects a trajectory to be acquired based on the imaging time and the candidate trajectory (Step S2). For example, the processing circuitry 51 selects a trajectory to be acquired from among candidate trajectories included in the set 70 in accordance with a predetermined rule (hereinafter referred to as a selection rule) based on the imaging time set in Step S1. Specifically, first, the processing circuitry 51 determines the number of trajectories to be acquired in accordance with the imaging time. Next, the processing circuitry 51 selects the trajectories to be acquired for the determined number from the set 70 in accordance with the selection rule. As the selection rule, for example, it is preferable to select so that the angles between the trajectories to be acquired are substantially the same. For example, as shown in the middle part of FIG. 3, three candidate trajectories of substantially equal angles among the eight candidate trajectories, that is, first, fourth and seventh candidate trajectories are selected as trajectories to be acquired. In FIG. 3, the trajectory to be acquired is indicated by a solid line.

The trajectory to be acquired is set for each slice or volume or for each frame. In other words, the trajectory to be acquired is set for each image. The quality of image by the radial method is typically guaranteed by about 800 spokes. However, according to the present embodiment, it is possible to guarantee the same image quality by about 30 to 50 spokes per image. This is because the acquisition trajectories according to the present embodiment have substantially equal angular interval.

Next, the processing circuitry 51 generates mask data 91 based on the selected trajectory to be acquired (Step S3). As shown in the lower part of FIG. 3, the mask data 91 is numerical data in which a numerical value indicating that it is selected (in other words, data is acquired) or a numerical value indicating that it is not selected (in other words, data is not acquired) is the assigned for each of a plurality of candidate trajectories. For example, "1" is assigned as a numerical value indicating that it is selected, and "0" is assigned as a numerical value indicating that it is not selected. The processing circuitry 51 determines whether or not each candidate trajectory is selected, assigns "1" when it is selected, and assigns "0" when it is not selected. The numerical values of "0" or "1" are arranged in order of the trajectory number of the candidate trajectories. For example, in the case of FIG. 3, the mask data 91 is, (1, 0 0, 1, 0, 0, 1, 0) because the first, fourth and seventh candidate trajectories are selected, and the second, third, fifth, sixth and eighth candidate trajectories are not selected.

When Step S3 is performed, the processing circuitry 51 executes the raw data acquisition function 513 (Step S4). In Step S4, the processing circuitry 51 instructs the sequence control circuitry 29 to execute MR imaging. The sequence control circuitry 29 synchronously controls the gradient field power supply 21, the transmitting circuitry 23 and the receiving circuitry 25, performs MR imaging on the trajectory to be acquired selected in Step S2, and acquires k-space data on the trajectory to be acquired. The k-space data acquired is k-space data corresponding to the trajectory to be acquired represented by the mask data generated in Step S3. Since the trajectory to be acquired is selected from among candidate trajectories for the number of the elements, the k-space data acquired in Step S4 is typically sparse.

When Step S4 is performed, the processing circuitry 51 executes the image generating function 514 (Step S5). In Step S5, the processing circuitry 51 performs DNN reconstruction on the mask data generated in Step S3 and the k-space data acquired in Step S4 to generate an MR image.

Figure 5:
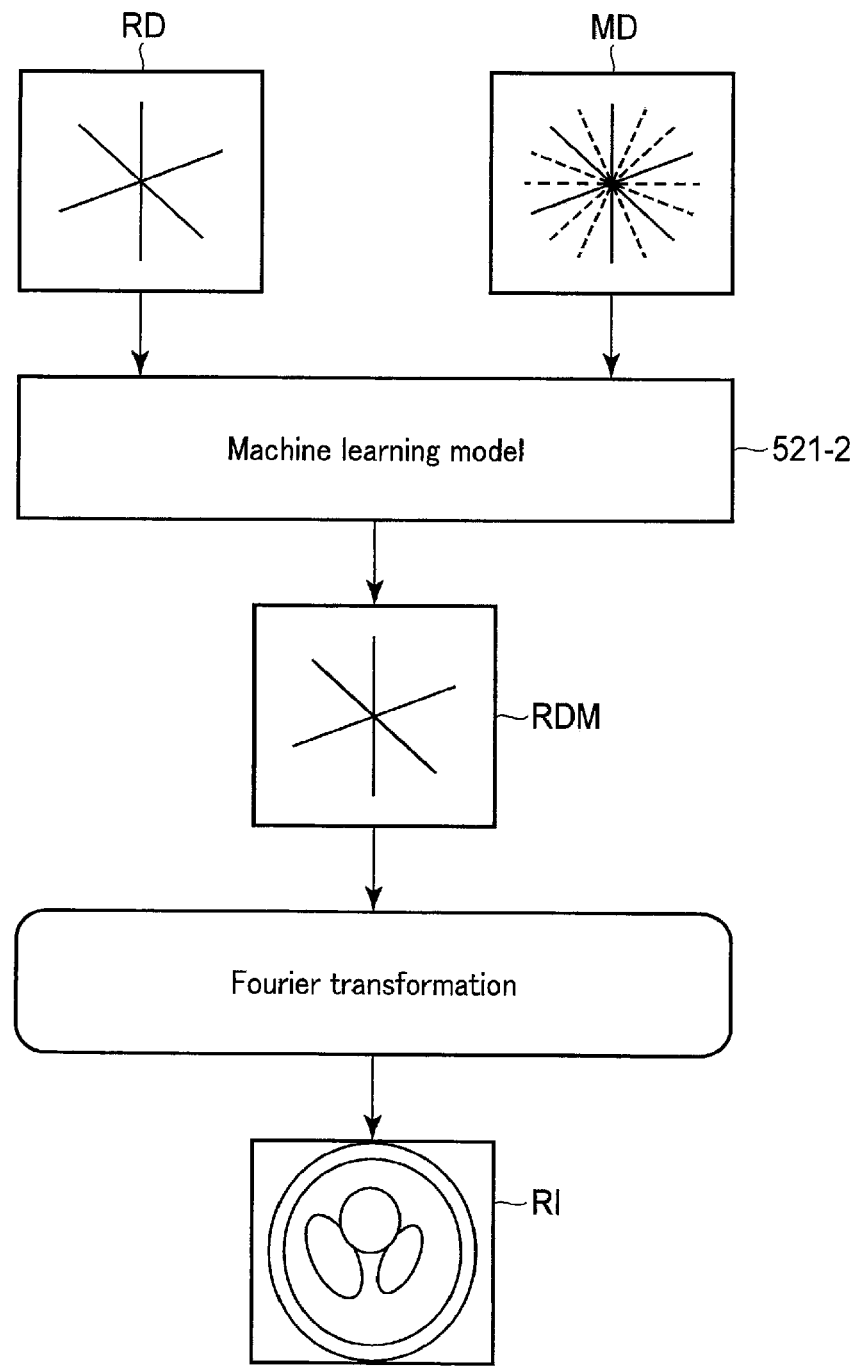
FIG. 5 is a drawing schematically showing a flow of the second DNN reconstruction according to the present embodiment.
Figure 6:
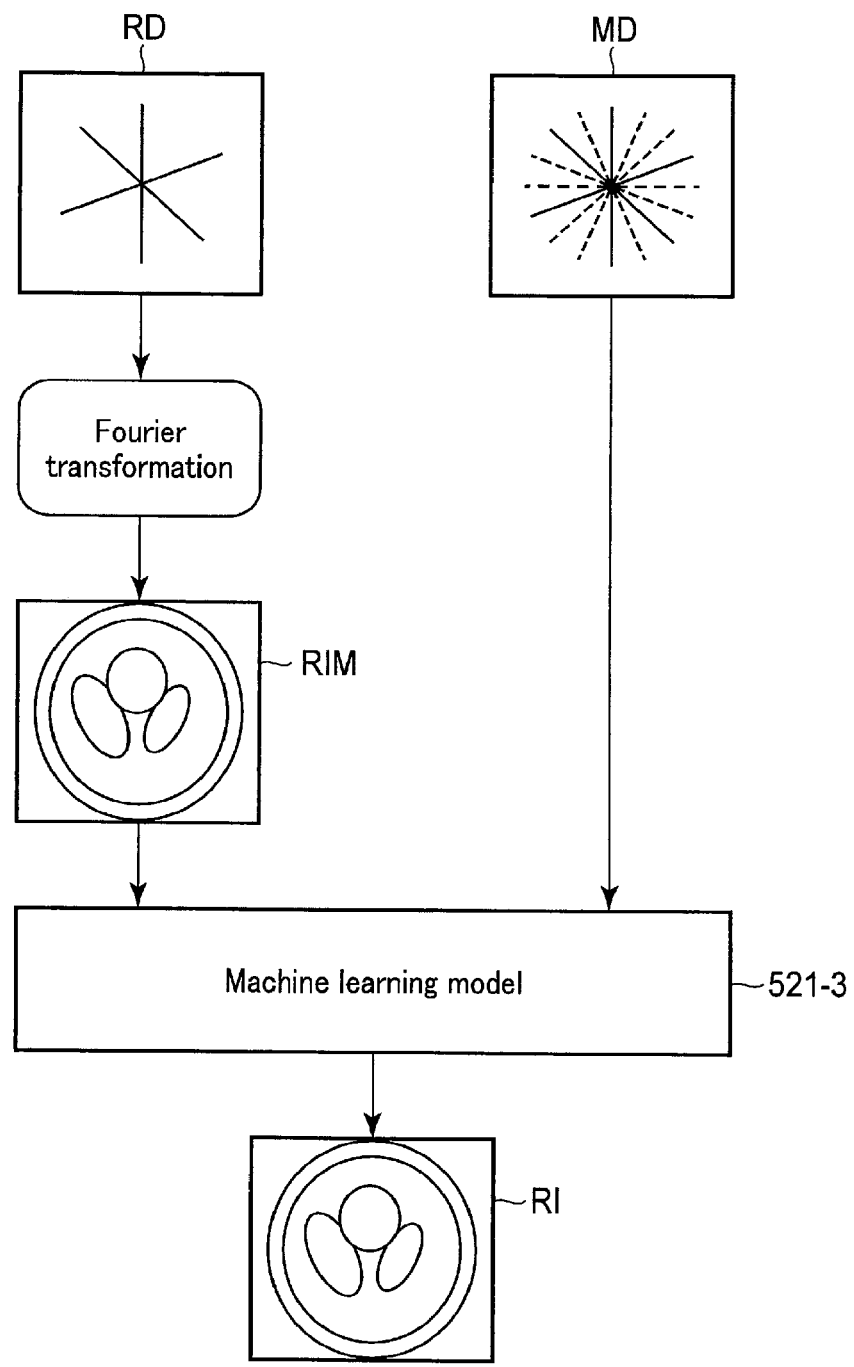
FIG. 6 is a drawing schematically showing a flow of a third DNN reconstruction according to the present embodiment.

FIG. 4, FIG. 5 and FIG. 6 are drawing schematically showing flows of DNN reconstruction according to the present embodiment. In the first DNN reconstruction shown in FIG. 4, the processing circuitry 51 applies the machine learning model 521-1 to the k-space data RD and the mask data MD, and generates an MR image RI corresponding to the k-space data RD. The machine learning model 521-1 receives k-space data and mask data, and the parameters are learned so as to output an MR image corresponding to the k-space data. The structure of the machine learning model 521-1 is not particularly limited. Artifacts due to signal deficiency included in the k-space data RD are reduced more in the MR image RI generated by the machine learning model 521-1 based on the k-space data RD and the mask data MD as compared to the MR image generated by an analytical reconstruction method such as Fourier transformation on the k-space data RD. This is because the machine learning model 521-1 uses mask data MD indicating a trajectory to be acquired corresponding to the k-space data RD as an input in addition to the k-space data RD.

It should be noted that the signal deficiency according to the present embodiment is a concept including any difference between actual k-space data and desired k-space data, including sparse. For example, signal deficiency includes not only sparse but also signal deterioration due to noise caused by various causes, information deficiency due to conversion from a continuous value to a discrete value generated in the process of A/D conversion, and the like.

In the second DNN reconstruction shown in FIG. 5, the processing circuitry 51 applies the machine learning model 521-2 to the k-space data RD and the mask data MD, and generate a k-space data RDM with the deficient part of signal included in the k-space data RD restored. The machine learning model 521-2 receives k-space data and mask data, and the parameters are learned so as to output de-noised k-space data. The k-space data RDM generated by the machine learning model 521-2 based on the k-space data RD and the mask data MD has reduced artifacts due to a signal deficiency included in the k-space data RD compared to the k-space data RD. This is because the machine learning model 521-2 uses mask data MD indicating a trajectory to be acquired corresponding to the k-space data RD as an input in addition to the k-space data RD.

As shown in FIG. 5, when the k-space data RDM is generated, the processing circuitry 51 performs Fourier transformation on the k-space data RDM to generate an MR image RI corresponding to the k-space data RD or the k-space data RDM. Since the MR image RI is generated by Fourier transformation of the k-space data RDM in which the deficient part of signal is restored, the image quality is improved compared to the MR image generated by the Fourier transformation of the k-space data RD including the signal deficiency.

In the third DNN reconstruction shown in FIG. 6, the processing circuitry 51 subjects the k-space data RD to Fourier transformation to generate a provisional MR image RIM corresponding to the k-space data RD. Since the provisional MR image RIM is a reconstructed image generated by performing Fourier transformation on k-space data RD including a signal deficiency, the provisional MR image RIM includes many signal deficiencies.

As shown in FIG. 6, when the provisional MR image RIM is generated, the processing circuitry 51 applies the machine learning model 521-3 to the provisional MR image RIM and the mask data MD, and the signals included in the provisional MR image RIM generates the MR image RI in which the deficient part of signal is restored. The machine learning model 521-3 learns the parameters so that the provisional MR image RIM and the mask data MD, are input and a de-noised MR image is output. The MR image RI generated by the machine learning model 521-3 based on the provisional MR image RIM and the mask data MD has reduced artifacts caused by the signal deficiency as compared to the provisional MR image RIM. This is because the machine learning model 521-3 uses mask data MD indicating a trajectory to be acquired corresponding to the k-space data RD used in the provisional MR image RIM as an input in addition to the provisional MR image RIM.

When Step S5 is performed, the processing circuitry 51 executes the display control function 516 (Step S6). In Step S6, the processing circuitry 51 displays the MR image generated in Step S5 on the display 53.

With the procedure described thus far, the MR imaging by the processing circuitry 51 is completed.

It should be noted that the flow of the process shown in FIG. 2 is an example, and the present embodiment is not limited thereto. For example, in Step S2, the processing circuitry 51 automatically selects the trajectory to be acquired based on the imaging time. However, the present embodiment is not limited thereto. For example, the processing circuitry 51 may select a candidate trajectory specified by the user via the input interface 54 as a trajectory to be acquired. In this case, for example, the processing circuitry 51 displays a schematic drawing which graphically represents selectable candidate trajectories of a limited number of the elements in a selectable manner on the display 53. As a schematic drawing, for example, an image in which candidate trajectories disposed in the k-space and their trajectory numbers are drawn as shown in the upper part of FIG. 3 is preferable. The user designates an arbitrary trajectory as the trajectory to be acquired from among the candidate trajectories included in the displayed schematic drawing via the input interface 54. The processing circuitry 51 may select the designated trajectory as the trajectory to be acquired.

The above embodiment is based on the assumption that one or zero times of data acquisition is performed for each trajectory to be acquired for MR imaging of one image. However, the present embodiment is not limited thereto. For example, data acquisition may be performed twice or more for a certain trajectory to be acquired. By performing data acquisition two or more times, the reliability of k-space data related to the trajectory to be acquired can be improved. For example, when data acquisition is performed twice for the first and fourth trajectories, once for the second, fifth and seventh trajectories, and zero time for the third, sixth and eighth trajectories, mask data will be (2, 1, 0, 2, 1, 0, 1, 0).

In the mask data according to the above embodiment, it is assumed that a numerical value corresponding to the number of times of acquisition is assigned to each data acquisition trajectory. However, the present embodiment is not limited thereto. For example, the numerical value "1" may be uniformly assigned to a data acquisition trajectory in which acquisition is performed twice or more. In addition, the numerical value "1" may be assigned in the case of 0 times and 2 or more times, and the numerical value "0" may be assigned in the case of 1 time. Arbitrary numerical values may be assigned to the mask data according to the present embodiment in accordance with other rules.

It should be noted that although the non-negative value is used as the mask data in the description of the present embodiment, the present invention is not limited thereto, and a negative value, for example, −1 may be included.

Also, the numerical value of the mask data is assumed to have a value corresponding to the number of times of acquisition. However, the present embodiment is not limited thereto. For example, a case where the same trajectory is acquired in the positive direction and the negative direction in the radial acquisition is considered. When the data acquisition trajectory in the positive direction and the data acquisition trajectory in the negative direction are treated as different trajectories, numerical values corresponding to the number of times of acquisition are assigned to each data acquisition trajectory. Without making distinction between data acquisition trajectories in the positive direction and data acquisition trajectories in the negative direction, a numerical value according to the acquisition direction or a numerical value according to the combination of the number of times of acquisition and the direction of acquisition may be assigned to one data acquisition trajectory. For example, in the case of acquiring 100 times each in the positive direction and the negative direction with respect to a 0° data acquisition trajectory, (1, 0) or the like is assigned to the data acquisition trajectory. It should be noted that "1" in (1, 0) is an example of the numerical value indicating a positive direction, and "0" is an example of a numerical value indicating a negative direction.

The structure of the machine learning model 521 can be changed in design as appropriate. For example, in the case of the second DNN reconstruction, the machine learning model 521 may incorporate an FFT (Fast Fourier Transfer) layer after an arbitrary multi-layer network (hereinafter, referred to as the present network layer) which inputs k-space data RD and mask data MD and outputs k-space data RDM. The k-space data is input to the FFT layer, the FFT is applied to the input k-space data, and an MR image is output. Accordingly, the machine learning model 521 alone can output the MR image RI based on the k-space data RD and the mask data MD.

The machine learning model 521 may also have a chain structure in which unit network structures including an Inverse Fast Fourier Transfer (IFFT) layer following the present network layer and the FFT layer are cascaded. An MR image is input to the IFFT layer, IFFT is applied to the input MR image, and k-space data is output. The chain structure can improve the restoration accuracy of the deficient part of signal.

In the chain structure, a matching layer may be provided after the IFFT layer. K-space data based on the MR image output from the present network layer and k-space data before processing input to the present network layer are input to the matching layer, and matching processing is performed on the completed k-space data using the k-space data before processing, and the k-space data after the matching processing is completed is output. The k-space data completed in the matching processing, the k-space data before processing is weighted and added for each pixel according to the degree of signal deficiency. For example, the lower the signal deficiency degree, the higher the weight given to the pixel value of the k-space data before processing, and the higher the signal deficiency degree, the lower the weight is given to the pixel value of the k-space data before processing. Accordingly, the consistency between the processed k-space data and the k-space data before processing can be secured.

Also, in the machine learning model 521, an element product operation layer may be provided in the previous stage of the present network layer. The element product operation layer calculates an element product of k-space data and mask data, and outputs element product data. The present network layer receives k-space data and element product data, and outputs MR image data in which a deficient part of signal of the k-space data is restored. The unit network structure of the present network layer and the element product operation layer may be cascaded.

In the above description, the k-space data input to the machine learning model 521 is the original k-space data acquired by MR imaging. However, the present embodiment is not limited thereto. The k-space data according to the present embodiment may be computational k-space data generated by performing forward projection processing on an MR image. Further, the k-space data or MR image according to the present embodiment may be raw data subjected to any signal processing such as signal compression processing, resolution decomposition processing, signal interpolation processing, resolution synthesis processing and the like. The raw data according to the present embodiment may be hybrid data generated by performing Fourier transformation on k-space data in the readout direction.

Next, learning of the machine learning model 521 will be described. The machine learning model 521 is generated by a model learning apparatus. The model learning apparatus causes the machine learning model to perform machine learning according to a model learning program based on training data including a plurality of training samples, and generates a learned machine learning model (hereinafter referred to as a learned model). The model learning apparatus is a computer such as a workstation having a processor such as a CPU and a GPU. The model learning apparatus and the medical information processing apparatus 50 may or may not be communicably connected via a cable or a communication network. In addition, the model learning apparatus and the medical information processing apparatus 50 may be configured by an integrated computer.

Figure 7:
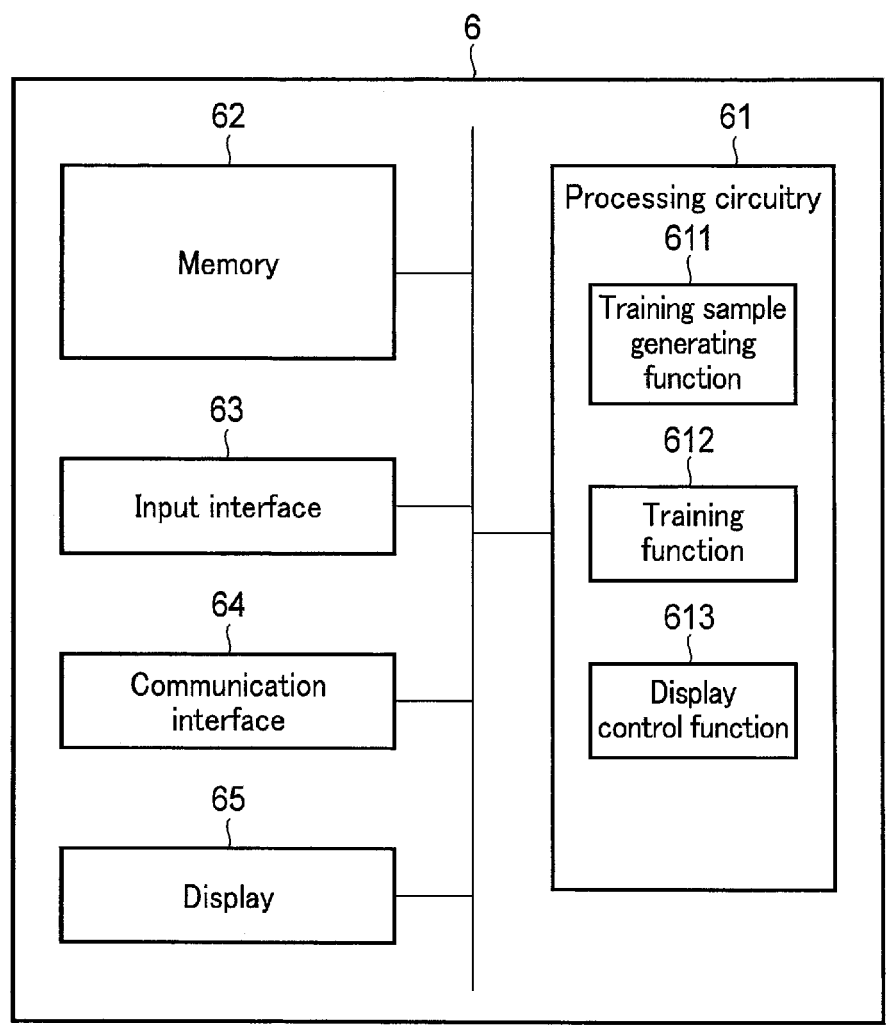
FIG. 7 is a drawing showing a configuration of a model learning apparatus according to the present embodiment.

FIG. 7 is a drawing showing the configuration of a model learning apparatus 6 according to the present embodiment. As shown in FIG. 7, the model learning apparatus 6 includes a processing circuitry 61, a memory 62, an input interface 63, a communication interface 64, and a display 65.

The processing circuitry 61 includes a processor such as a CPU or a GPU. The processor executes a training sample generating function 611, a training function 612, a display control function 613 and the like by activating a model learning program installed in the memory 62 and the like. It should be noted that the respective functions 611 to 613 are not limited to being realized by a single processing circuitry. A plurality of independent processors may be combined to constitute a processing circuitry, and each processor may execute a program to realize each of the functions 611 to 613.

In the training sample generating function 611, the processing circuitry 61 generates a training sample which is a combination of input data and output data. The processing circuitry 61 generates training samples based on k-space data acquired along all candidate trajectories.

In the training function 612, the processing circuitry 61 causes the machine learning model to train parameters based on training data on a plurality of training samples. By training parameters by the training function 612, a learned machine learning model 521 shown in FIG. 1 is generated.

In the display control function 613, the processing circuitry 61 displays the training data, the learning result and the like on the display 65.

The memory 62 is a storage apparatus such as a ROM, a RAM, an HDD, an SSD, an integrated circuitry storage apparatus, and the like for storing various information. The memory 62 stores, for example, a model learning program for learning a multi-layered network. The memory 62 may be a drive apparatus for reading and writing various information from/to a portable storage medium such as a CD, a DVD, a flash memory, or a semiconductor memory device such as a RAM, in addition to the storage apparatus. Also, the memory 62 may be in another computer Connected to the model learning apparatus 6 via a network.

The input interface 63 receives various input operations from the user, converts the received input operations into electrical signals, and outputs the electric signals to the processing circuitry 61. Specifically, the input interface 63 is connected to input apparatuses such as a mouse, a keyboard, a trackball, a switch, a button, a joystick, a touch pad, and a touch panel display. The input interface 63 outputs an electrical signal corresponding to the input operation to the input apparatus to the processing circuitry 61. The input apparatus connected to the input interface 63 may be an input apparatus provided in another computer connected via a network or the like.

The communication interface 64 is an interface for performing data communication with the medical information processing apparatus 50, the medical image diagnostic apparatus, and another computer.

The display 65 displays various information in accordance with the display control function 613 of the processing circuitry 61. For example, the display 65 displays training data, learning results, and the like. The display 65 also outputs a GUI or the like for receiving various operations from the user. For example, as the display 65, a liquid crystal display, a CRT display, an organic EL display, a plasma display, or any other display can be appropriately used.

Next, an operation example of the model learning apparatus 6 according to the present embodiment will be described.

As described above, the processing circuitry 61 generates training samples based on k-space data acquired along all candidate trajectories. The types of input data and output data differ depending on the type of machine learning model 521 shown in FIG. 4, FIG. 5 and FIG. 6. In the case of the machine learning model 521-1 of FIG. 4, mask data and k-space data including signal deficiency are used as input data, and an MR image with reduced signal deficiency is used as output data. In the case of the machine learning model 521-2 of FIG. 5, mask data and k-space data including signal deficiency are used as input data, and k-space data with reduced signal deficiency is used as output data. In the case of the machine learning model 521-3 of FIG. 6, mask data and MR image including signal deficiency are used as input data, and an MR image with reduced signal deficiency is used as output data.

Hereinafter, as an example of the machine learning model 521, machine learning processing will be described with an example of the machine learning model 521-1 in FIG. 4 in which parameters are learned so as to output an MR image by inputting k-space data and mask data.

FIG. 8 is a drawing schematically showing processing executed by the training sample generating function 611. As shown in FIG. 8, full k-space data RDF is acquired by the processing circuitry 61. The full k-space data is k-space data obtained by acquiring data for all candidate trajectories of a finite number of elements. The full k-space data RDF is acquired in advance by the magnetic resonance imaging apparatus 1 or the like.

As shown in FIG. 8, in the training sample generating function 611, the processing circuitry 61 performs under-sampling processing on the full k-space data RDF, and generates virtual k-space data RD1 to RDn for all combinations of processing target trajectories (hereinafter referred to as trajectory combinations). For example, the processing circuitry 61 calculates k-space data corresponding to each trajectory combination by simulation based on the full k-space data RDF. In FIG. 8, virtual k-space data RD1 to RDn illustrate k-space data relating to three processing target trajectories, but the number of processing target trajectories constituting virtual k-space data RD1 to RDn may be any number as long as it is smaller than the number of candidate trajectories constituting the full k-space data RDF. The virtual k-space data RD1 to RDn are used as input data of the machine learning model 521-1.

When under-sampling processing is performed, the processing circuitry 61 performs Fourier transformation on each of the virtual k-space data RD1 to RDn to generate virtual MR images RI1 to RIn corresponding to the virtual k-space data RD1 to RDn. The virtual MR images RI1 to RIn are used as correct MR images of the machine learning model 521-1.

The processing circuitry 61 performs mask data conversion processing on each of the virtual k-space data RD1 to RDn, and generates mask data MD1 to MDn corresponding to the virtual k-space data RD1 to RDn. Specifically, the processing circuitry 61 first specifies the trajectory combination of each of the virtual k-space data RD1 to RDn. Then, for each candidate trajectory, the processing circuitry 61 assigns a numerical value "1" to the trajectory included in the trajectory combination and assigns a numerical value "0" to a trajectory not included in the trajectory combination. Thereby, mask data MD1 to MDn are generated. The mask data MD1 to MDn are used as input data of the machine learning model 521-1.

The mask data MD1 to MDn, the k-space data RD1 to RDn, and the MR images RI1 to RIn are associated with each other for each trajectory combination. The mask data MD1 to MDn, the k-space data RD1 to RDn, and the MR images RI1 to RIn for each trajectory combination are treated as training samples. The training samples for each trajectory combination are stored in the memory 62.

Accordingly, the processing by the training sample generating function 611 ends. Next, training processing by the training function 612 is performed. In the training function 612, the processing circuitry 61 applies k-space data RD1 to RDn and mask data MD1 to MDn to the machine learning model to perform forward propagation processing for each trajectory combination, and outputs MR image (hereinafter referred to as estimated MR image). Next, the processing circuitry 61 applies the difference (error) between an estimated MR result and the correct MR image to the machine learning model to perform back propagation processing, and calculates a gradient vector. Next, the processing circuitry 61 updates parameters such as a weighting matrix and a bias of the machine learning model based on the gradient vector. By repeating the forward propagation processing, the back propagation processing, and parameter updating processing while changing the training sample, a learned machine learning model 521-1 is generated.

The learned machine learning model 521-1 is stored in the memory 62. Also, the learned machine learning model 521-1 is transmitted to the magnetic resonance imaging apparatus 1 via the communication interface 64.

As described above, the type of the k-space filling method according to the present embodiment may be a spiral method. Also in this case, mask data can be generated as in the radial method. The candidate trajectory relating to the spiral method draws a spiral starting from the center of k-space and ending at an arbitrary point. Similar to the radial method, the processing circuitry 51 selects an arbitrary candidate trajectory from among a set including a plurality of candidate trajectories as a trajectory to be acquired, and generates mask data corresponding to the selected trajectory to be acquired. It should be noted that since the candidate trajectories that can be generated depend on hardware performance of the gradient coil, it is necessary to prepare training data for each target hardware. Alternatively, a set of candidate trajectories of the spiral method may be defined in accordance with low gradient coils so as to be compatible with a plurality of hardware.

In the above description, the medical information processing apparatus 50 is incorporated in the magnetic resonance imaging apparatus 1. However, the present embodiment is not limited thereto.

FIG. 9 is a view showing another configuration of the medical information processing apparatus 50 according to the present embodiment. As shown in FIG. 9, the medical information processing apparatus 50 is a single computer independent of a modality apparatus such as a magnetic resonance imaging apparatus. Similar to the medical information processing apparatus 50 of FIG. 1, the medical information processing apparatus 50 of FIG. 9 includes a processing circuitry 51, a memory 52, a display 53, an input interface 54, and a communication interface 55. The functions and the like of each configuration are the same as those in FIG. 1.

It should be noted that the medical information processing apparatus 50 of FIG. 9 can process raw data acquired by any modality apparatus. For example, the raw data may be sinogram data acquired by an x-ray computed tomography apparatus.

As described above, the medical information processing apparatus 50 according to the present embodiment has the processing circuitry 51. The processing circuitry 51 implements at least a mask data acquisition function 512, a raw data acquisition function 513, and an image generating function 514. In the mask data acquisition function 512, the processing circuitry 51 acquires mask data in which numerical values corresponding to the number of times of acquisition and/or the direction of acquisition in target imaging are assigned to a plurality of data acquisition trajectory candidates having a finite number of elements. In the raw data acquisition function 513, the processing circuitry 51 acquires the raw data acquired in the target imaging on the subject P. In the image generating function 514, the processing circuitry 51 performs reconstruction processing using the machine learning model 521 on the acquired mask data and the acquired raw data to generate a medical image on the subject P.

According to the above configuration, the machine learning model 521 uses, in addition to the k-space data, mask data indicating a trajectory to be acquired corresponding to the k-space data as an input. Thus, the image quality of the output medical image can be improved as compared to a case where only the k-space data is input. Further, since the candidate trajectories are limited to trajectories having a predetermined finite number of elements, it is not necessary to calculate the trajectories to be acquired for each MR imaging. In relation to this, it is possible to easily match the data acquisition trajectory used for training data and the data acquisition trajectory used for MR imaging.

In the above embodiment, the input of the machine learning model is medical data such as raw data or medical image and mask data to which numerical values according to the number of times of acquisition and/or the direction of acquisition in target imaging for a plurality of data acquisition trajectory candidates having a finite number of elements are assigned. However, the present embodiment is not limited thereto. The concept of mask data can be extended to numerical data obtained by digitizing acquisition condition for medical data. The acquisition condition for medical data is a concept including not only an imaging protocol for medical imaging but also data processing conditions for raw data and image processing conditions for medical images. The imaging protocol for medical imaging includes not only the data acquisition trajectory described above, but also the type of pulse sequence, a frame number, and a type of k-space filling trajectory.

In the above embodiment, the machine learning model is used for DNN reconstruction from raw data to medical images. However, the present embodiment is not limited thereto. The output of the machine learning model may be any data as long as it is data used for medical diagnosis. For example, a machine learning model may be configured to output results of identification such as restoration of a deficient part of raw data, restoration of a deficient part of a medical image, generation of a segmentation image in which an anatomical tissue or the like is segmented, and the anatomical tissue.

FIG. 10 is a drawing schematically showing numerical data 93; Numerical data 93 shown in FIG. 10 is data obtained by digitizing the type of pulse sequence. As shown in FIG. 10, the numerical data 93 includes elements 94 for two or more finite number of elements. The number of the elements matches the number of a plurality of candidate conditions included in the category to which the acquisition condition to be digitized belongs. For example, as shown in FIG. 10, when the category of the acquisition condition to be digitized is the type of pulse sequence, examples of candidate conditions include three types; FSE (Fast Spin Echo), FE (Field Echo) and EPI (Echo Planar Imaging). In this case, the numerical data 93 is expressed as (FSE, FE, EPI).

Each element 94 corresponds to a numerical value corresponding to whether or not each of a plurality of candidate conditions is adopted by the acquisition condition of the target imaging. For example, as the value of the element 94, one of a first value indicating that the candidate condition in question is adopted and a second value indicating that the candidate condition in question is not adopted is assigned. In this case, the numerical data 93 is referred to as one-hot vector. Any integer or natural number may be used as long as the first value and the second value are different values. For example, the first value is set to "1" and the second value is set to "0".

For example, as shown in FIG. 10, when the acquisition condition of the target imaging adopts FSE is adopted, the value of the element 84 corresponding to FSE is set to "1", the value of the element 84 corresponding to FE is set to "0", and the value of the element 84 corresponding to EPI is set to "0". It should be noted that the number of the elements may be any number of finite or infinite. In other words, the number of candidate conditions may be any number. For example, it is possible to set the number of the elements, that is, the number of candidate conditions to one million or more.

Figure 11:
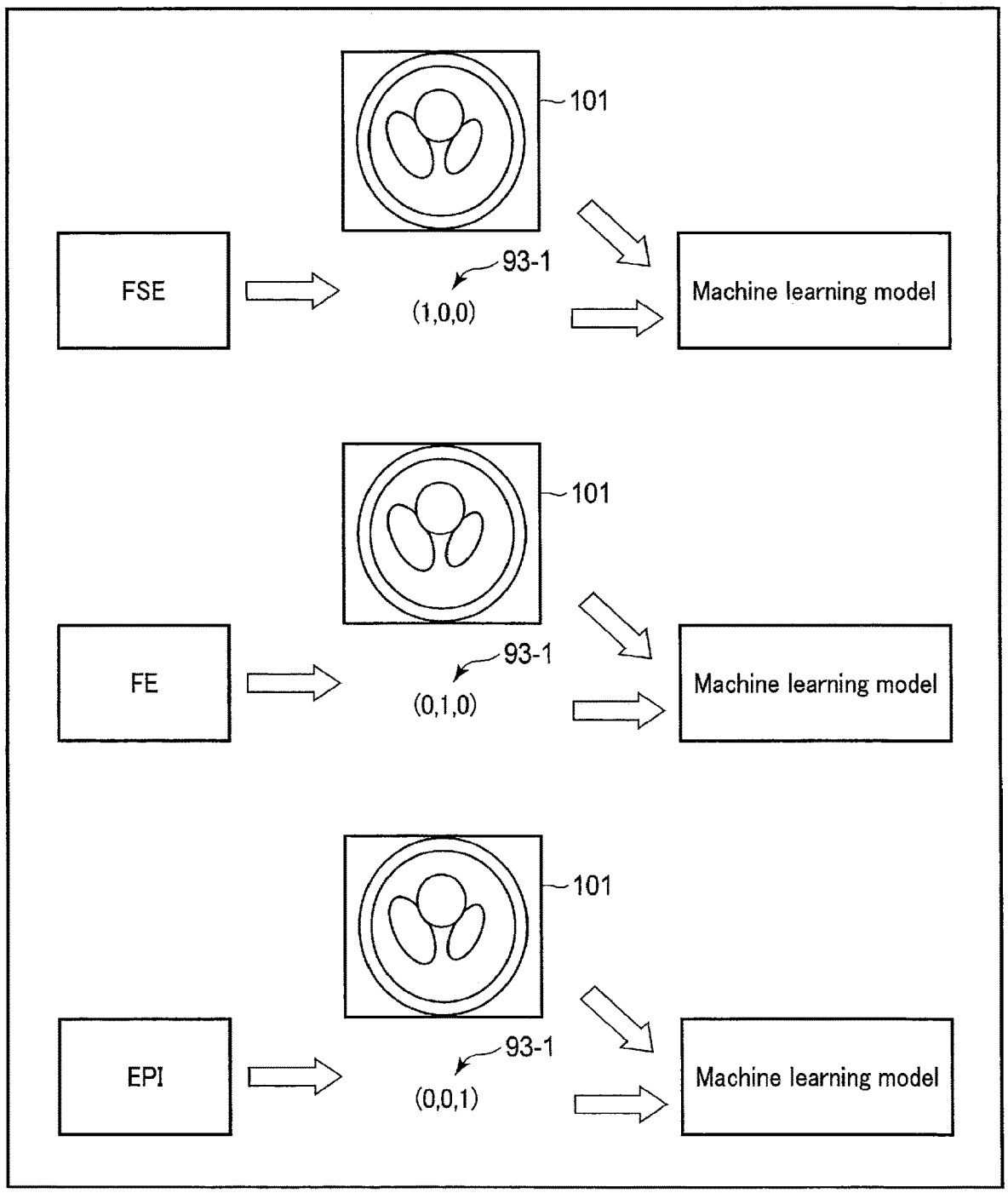
FIG. 11 is a drawing schematically showing an input of the numerical data of FIG. 10 to a machine learning model.

FIG. 11 is a drawing schematically showing an input of the numerical data 93-1 of FIG. 10 to a machine learning model. As shown in the upper part of FIG. 11, when FSE is adopted, the value of the element corresponding to FSE of numerical data 93-1 is "1", the value of the element corresponding to FE is "0", and EPI corresponds. The value of the element is set to "0". A combination of the numerical data 93-1 and the input medical image 101 is input to the machine learning model. As shown in the middle part of FIG. 11, when FE is adopted, the value of the element corresponding to FE of numerical data 93-1 is set to "0", the value of the element corresponding to FE is set to "1", and the value of the element corresponding to EPI is set to "0". A combination of the numerical data 93-1 and the input medical image 101 is input to the machine learning model. As shown in the lower part of FIG. 11, when EPI is adopted, the value of the element corresponding to EPI of numerical data 93-1 is "0", the value of the element corresponding to FE is "0", and the value of the element corresponding to EPI is set to "1". A combination of the numerical data 93-1 and the input medical image 101 is input to the machine learning model. By adding the numerical data 93-1 obtained by digitizing the type of pulse sequence in this manner to the input of the machine learning model, it becomes possible to generate output data taking the type of pulse sequence into consideration as well as the medical image or raw data. Therefore, the accuracy of the output data of the machine learning model is improved.

Figure 12:
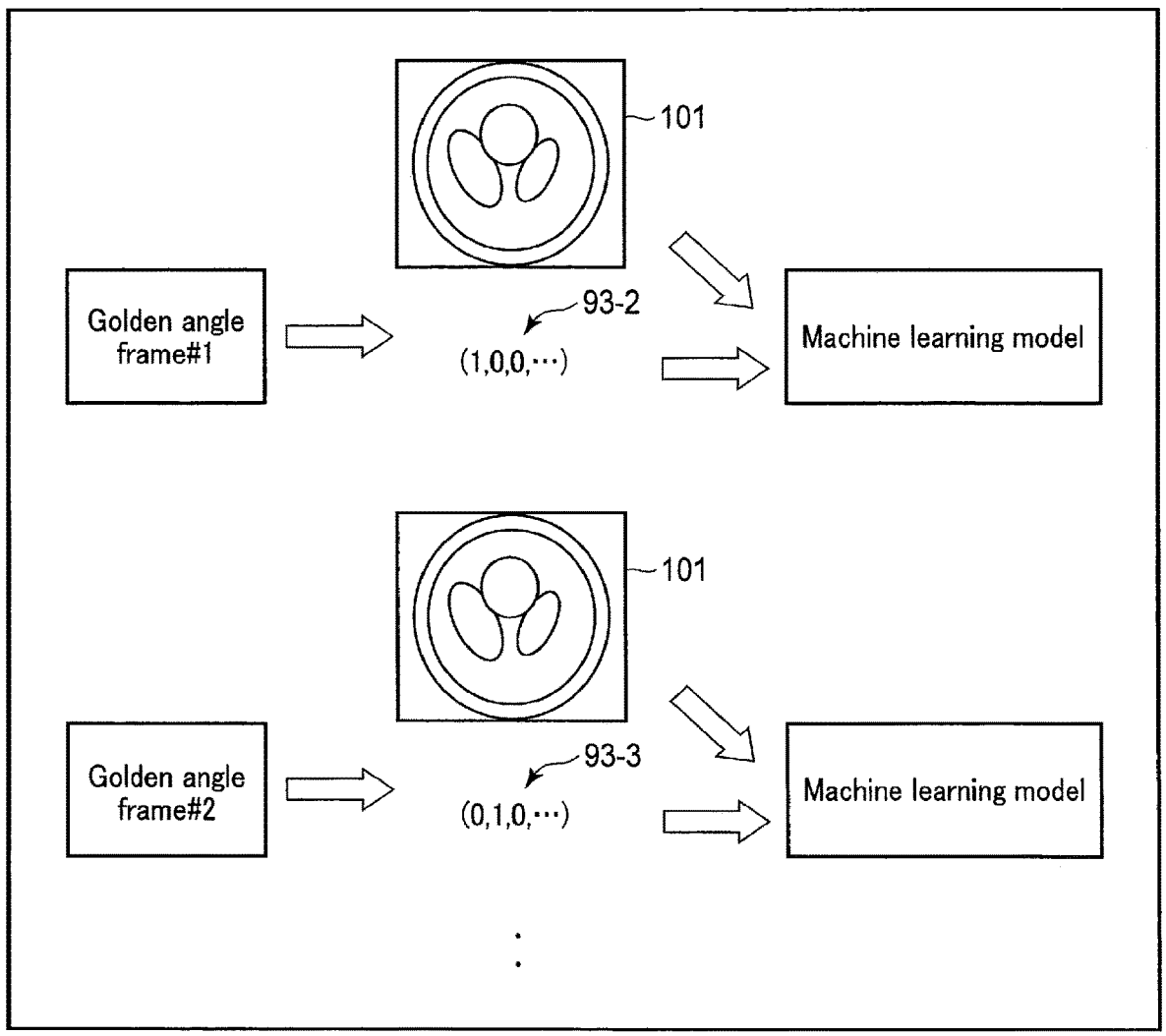
FIG. 12 is a drawing schematically showing an input of another numerical data to the machine learning model.

FIG. 12 is a drawing schematically showing the input of another numerical data 93-2 to the machine learning model. Numerical data 93-2 shown in FIG. 12 is a digitized acquisition condition "golden angle frame number". The golden angle frame number is a frame number of dynamic imaging using the radial method in which the acquisition angle of the data acquisition trajectory is set according to the rule of the golden angle, and the frame number is associated with the golden angle of the reference data acquisition trajectory relating the frame. The reference data acquisition trajectory is a data acquisition trajectory of any order, such as first, last, or intermediate, when the frame is constructed of a plurality of data acquisition trajectories. In this case, the numerical data 93-2 is expressed as (golden angle frame #1, golden angle frame #2, . . . ). The number of the elements of the numerical data 93-2 matches or corresponds to the number of frame number candidates.

As shown in the upper part of FIG. 12, when the input medical image 101 is the golden angle frame #1, the value of the element corresponding to the golden angle frame #1 of the numerical data is "1", and the value of the element corresponding to other frames is set to "0". A combination of the numerical data 93-2 and the input medical image 101 is input to the machine learning model. As shown in the middle part of FIG. 12, when the input medical image 101 is the golden angle frame #2, the value of the element corresponding to the golden angle frame #2 of the numerical data is "1", and the value of the element corresponding to other frames is set to "0". A combination of the numerical data 93-2 and the input medical image 101 is input to the machine learning model. By adding the numerical data obtained by digitizing the golden angle frame number in this manner to the input of the machine learning model, it becomes possible to generate output data taking the golden angle frame number into consideration as well as the medical image or raw data. Therefore, the accuracy of the output data of the machine learning model is improved.

It should be noted that the acquisition angle and acquisition order of data acquisition trajectories of the radial method in dynamic imaging are not limited to those using the golden angle, but may be those using an inverted bit pattern or those using a sequential pattern. In this case, the number of the elements of the numerical data matches or corresponds to the number of candidates for the inverted bit pattern or the sequential pattern. The value of each element is set according to whether or not the inverted bit pattern or the sequential pattern for the input medical image adopts the inverted bit pattern or the sequential pattern corresponding to the element.

Figure 13:
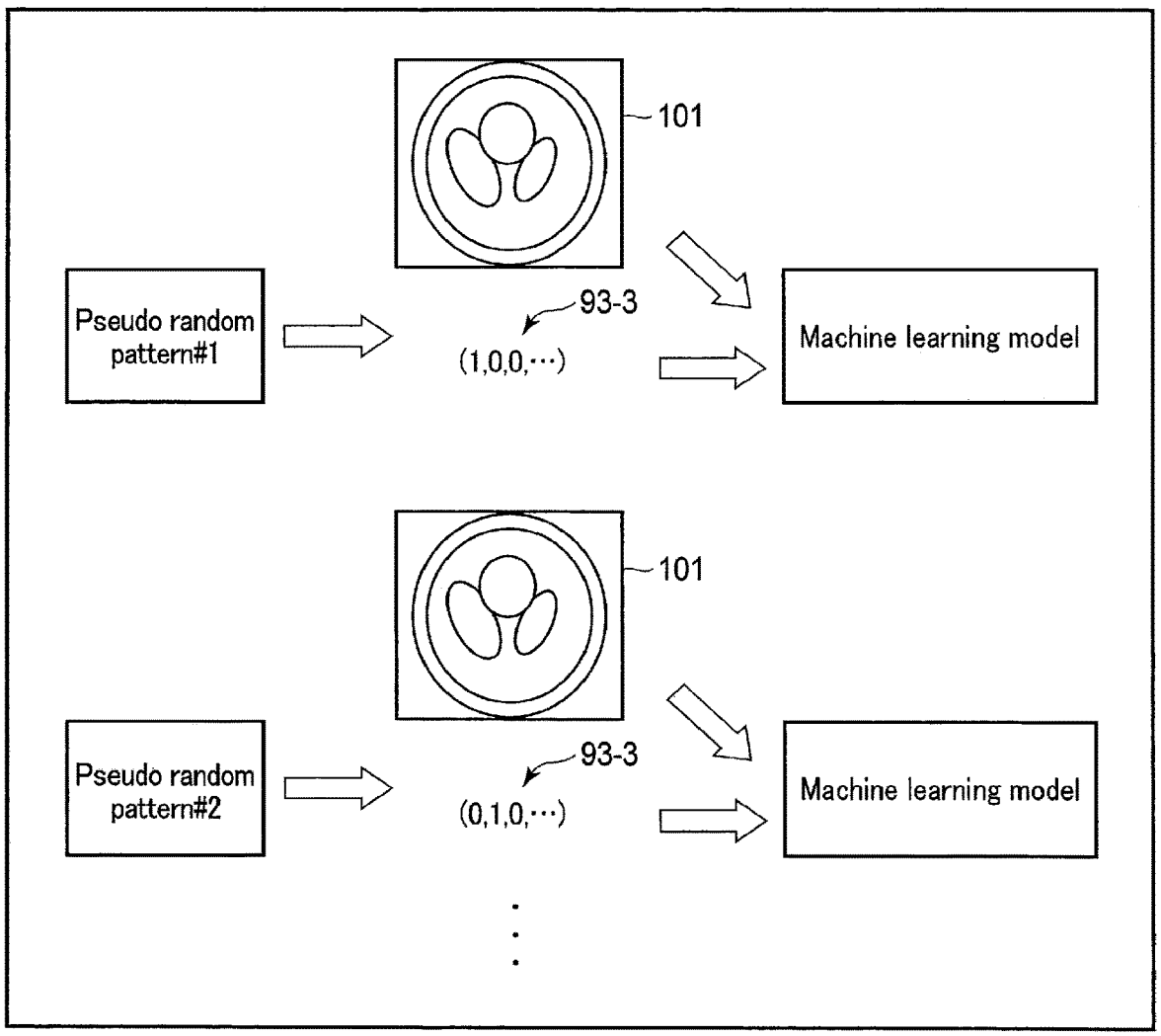
FIG. 13 is a drawing schematically showing an input of another numerical data to the machine learning model.

FIG. 13 is a drawing schematically showing the input of another numerical data 93-3 to the machine learning model. The numerical data 93-3 shown in FIG. 13 is obtained by digitizing acquisition condition "pseudo random pattern number". The pseudo random pattern number is a number of a random number pattern of dynamic imaging using the pseudo random Cartesian method, and the frame number is associated with the random number pattern related to the frame. It should be noted that the pseudo random Cartesian method refers to the Cartesian method in which a data acquisition trajectory is set according to a random number pattern. In this case, the numerical data 93-3 is expressed as (pseudo random pattern #1, pseudo random pattern #2, . . . ). The number of the elements of the numerical data 93-3 matches or corresponds to the number of candidates for the random number pattern.

As shown in the upper part of FIG. 13, when the input medical image 101 is the pseudo random pattern #1, the value of the element corresponding to the pseudo random pattern #1 of the numerical data 93-3 is "1", and the values of the elements corresponding to other pseudo random patterns are set to "0". A combination of the numerical data 93-3 and the input medical image 101 is input to the machine learning model. As shown in the middle part of FIG. 13, when the input medical image 101 is the pseudo random pattern #2, the value of the element corresponding to the pseudo random pattern #2 of the numerical data 93-3 is "1", and the elements corresponding to other pseudo random patterns are set to "0". A combination of the numerical data 93-3 and the input medical image 101 is input to the machine learning model. By adding the numerical data obtained by digitizing the pseudo random pattern number in this manner to the input of the machine learning model, it becomes possible to generate output data taking the golden angle frame number into consideration as well as the medical image or raw data. Therefore, the accuracy of the output data of the machine learning model is improved.

The acquisition conditions for dynamic (time-series) imaging, which are to be digitized, are not limited to those described above, and may be, for example, frame numbers defined by the cardiac phase. The frame number defined by the cardiac phase is, for example, the number of the cardiac phase of the frame when the R wave to the next R wave is 100%.

The acquisition condition to be digitized may be an acceleration factor of parallel imaging. In this case, the number of the elements of numerical data is defined as the number of candidates for the acceleration factor rate. The value of the element has a value according to whether or not the acceleration factor corresponding to the element is adopted in the target imaging. The artifacts resulting from parallel imaging have features according to the acceleration factor. Therefore, the machine learning model can detect the feature according to the acceleration factor by adding numerical data obtained by digitizing the acceleration factor of parallel imaging to the input of the machine learning model, and thus the accuracy of the output data of the machine learning model is enhanced.

The acquisition conditions to be digitized are not limited to the above, and may be, for example, data processing conditions for raw data or image processing conditions for medical images. As the data processing conditions or the image processing conditions, for example, there is the number of times of repetition of the repeat operation. The repeat operation is an operation such as noise removal processing, edge emphasis processing, smoothing processing and the like that is repeatedly applied to raw data or medical images, and the number of times of repetition is the number obtained by repeating the operation. Alternatively, the repeat operation is an operation for reducing the reconstruction error between the raw data and the reconstructed image when reconstructing the medical image from raw data, and the number of times of repetition is the number of times of repeating the operation when the operation is performed alternately. The operation is performed using a filter, DNN or the like. The number of the elements of the numerical data is defined as the number of candidates for the number of times of repetition, and the value of the element has a value corresponding to whether or not the target operation is repeated by the number of times of repetition corresponding to the element. As described above, by adding medical data after the repeat operations and numerical data obtained by digitizing the number of times of repetition of repeated operation to the input of the machine learning model, it is possible to generate output data considering not only the medical data but also the number of times of repetition. Therefore, the accuracy of the output data of the machine learning model is improved. It should be noted that the number of times of repetition may be a one-hot vector. Alternatively, the number of times of repetition may be a vector given in the form of a one-hot vector for the first few times (for example, three times) and given as the number of times of repetition beyond that number of times.

Numerical data relating to data processing conditions or image processing conditions may be digitized data which expresses whether or not a plurality of types of data processing or image processing are adopted. In this case, the number of the elements of numerical data is the number of candidates for data processing or image processing, and the value of each element is set to a value according to whether or not individual data processing or image processing is adopted. For example, numerical data may be expressed as (noise reduction, edge emphasis, segment processing) or the like.

The number of the elements of the above numerical data is assumed to match the number of candidate conditions. However, the present embodiment is not limited thereto.

Figure 14:
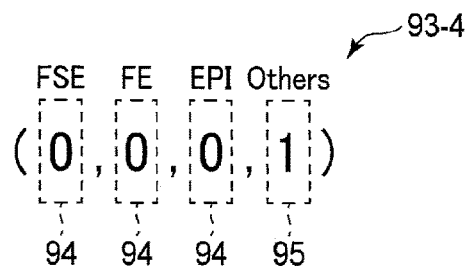
FIG. 14 is a drawing schematically showing another numerical data.

FIG. 14 is a view schematically showing another numerical data 93-4. As shown in FIG. 14, the numerical data 93-4 includes an element 94 corresponding to any of the candidate conditions and an element 95 corresponding to the fact that none of the candidate conditions is met. For example, the value of the element 95 is set to "0" when it corresponds to any of the candidate conditions, and is set to "1" when it corresponds to any of the candidate conditions. For example, as shown in FIG. 14, when the numerical data 93-4 is data obtained by digitizing the pulse sequence and the pulse sequence of the actual MR imaging is not any of FSE, FE, and EPI, the value of the element 95 is set to "1". By providing the element 95 in the numerical data 93-4, it is possible to clearly indicate to the machine learning model that the pulse sequence of the actual MR imaging does not correspond to any of the candidate conditions.

It is assumed that the above numerical data is obtained by digitizing one type of acquisition condition such as the type of pulse sequence and frame number. However, the present embodiment is not limited thereto. For example, numerical data may represent the type of pulse sequence and the frame number as a vector of one column. In this case, the numerical data is specifically represented by (FSE, FE, EPI, frame number 1, frame number 2, . . . ) or the like.

Further, in the above description, it was assumed that the element of the numerical data was a one-hot vector representing whether or not the candidate condition in question is adopted in binary. However, the element may be a vector that represents multi-level concepts such as the strength, direction, and number of times of the candidate condition in question in three or more values.

Next, the network structure of the machine learning model according to the present embodiment will be described.

Figure 15:
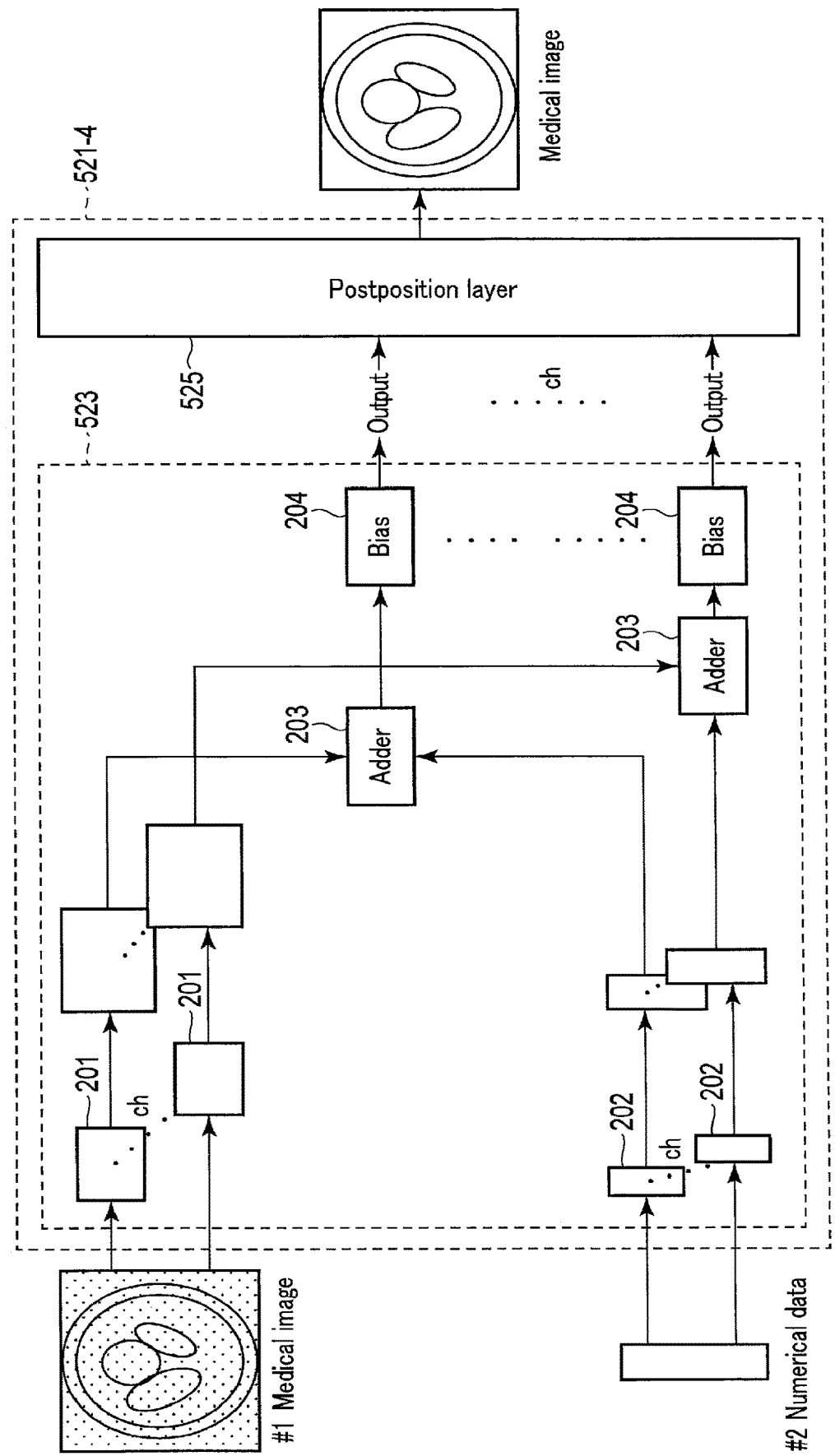
FIG. 15 is a drawing schematically showing a network structure of the machine learning model according to the present embodiment.

FIG. 15 is a view schematically showing a network structure of a machine learning model 521-4 according to the present embodiment. As shown in FIG. 15, it is assumed as an example that the machine learning model 521-4 is a DNN in which parameters has been trained to output a medical image having no noise, for example by inputting a combination of a medical image #1 having noise and numerical data #2 obtained by digitizing the acquisition condition for the medical image. It is assumed that there is one set each of the medical image #1 and the numerical data #2.

The machine learning model 521-4 has a CNN layer 523. The CNN layer 523 is configured to multiply each of the medical image #1 and the numerical data #2 by a weight different for each channel and add the product. For example, a plurality of filters with the number of channel ch are applied to medical image #1, and a plurality of filters with the same number of channels ch are applied to numerical data #2. The medical image and the numerical data after filtration are added for each channel by the adder 203 and converted into addition data. The addition data is converted into bias data by adding a constant value for each channel by the bias 204. Bias data for each channel is output from the CNN layer 523.

The network structure of the CNN layer 523 is an example, and various modifications are possible. For example, the CNN layer 523 may be provided with multi-stage filters 201 and 202 instead of the single-stage filters 201 and 202. For example, the size of the filter 201 may be set to 5×5, and the size of the filter 202 may be set to 1×1 or the like, but the size of the filters 201 and 202 may have any size.

Following the CNN layer 523 is a postposition layer 525. The postposition layer 525 performs an operation on the bias data for a plurality of channels from the CNN layer 523 and outputs a medical image having no noise as an output of the machine learning model 521-4. The postposition layer 525 has at least one or more fully connecting layers and an output layer, but in addition to these layers, it may have any layer such as one or more CNN layers, a pooling layer, and a normalization layer.

The input of the CNN layer 523 shown in FIG. 15 was assumed to be one set of medical image and one set of numerical data. However, the present embodiment is not limited thereto. The input of the CNN layer may be multiple sets of medical images and the same set of numerical data.

Figure 16:
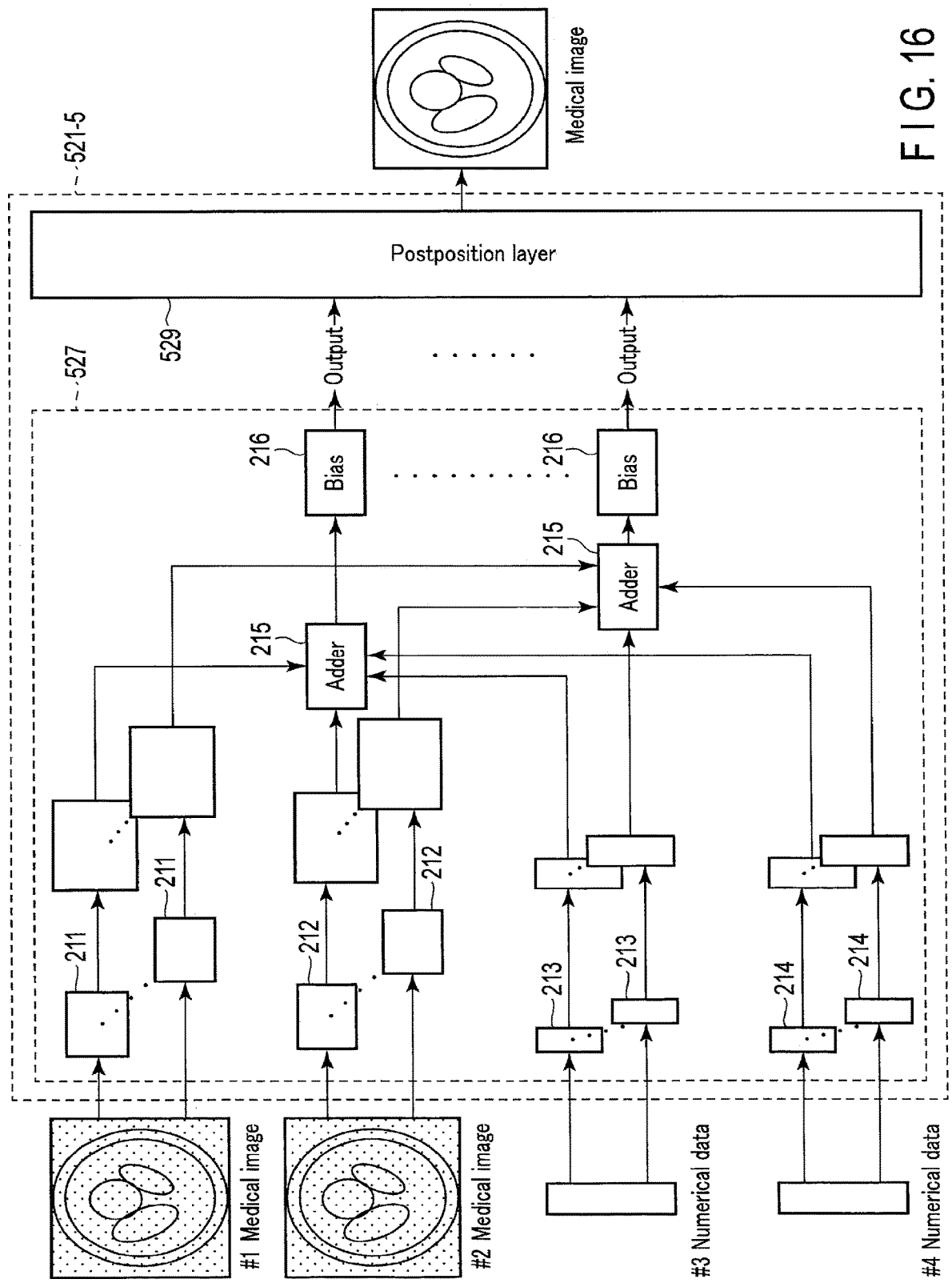
FIG. 16 is a drawing schematically showing a network structure of another machine learning model according to the present embodiment.

FIG. 16 is a drawing schematically showing a network structure of another machine learning model 521-5 according to the present embodiment. As shown in FIG. 16, it is assumed as an example that the machine learning model 521-5 is a DNN in which parameters has been trained to output a medical image having no noise, for example, when inputting a combination of a medical image #1 having noise, a medical image #2 having noise, numerical data #3 obtained by digitizing acquisition conditions relating to medical image #1 and numerical data #4 obtained by digitizing the acquisition condition relating to the medical image #2. The medical image #2 is, for example, a medical image derived from the medical image #1, such as a copy of the medical image #1 or a medical image obtained by performing arbitrary image processing on the medical image #1. The medical image 2 may be another medical image acquired under the same acquisition condition as that for the medical image #1, or may be a medical image acquired under another acquisition condition.

The machine learning model 521-5 has a CNN layer 527. The CNN layer 527 is configured to multiply the medical image #1, the medical image #2, the numerical data #3 and the numerical data #4 respectively by weights different for respective channels and add respective products. For example, a plurality of filters 211 by the number of channels ch are applied to medical image #1, a plurality of filters 212 by the same number ch are applied to medical image #2, a plurality of filters 213 of same number ch are applied to numerical data #3, and a plurality of filters 214 of the same number ch are applied to numerical data #4. The medical images and the numerical data after filtration are added for each channel by the adder 215 and converted into addition data. The addition data are converted into bias data by the bias 216 by being added with a constant value for the respective channels. Bias data for the respective channels are output from the CNN layer 527.

The network structure of the CNN layer 527 is an example, and various modifications are possible. For example, the CNN layer 527 may be provided with multi-stage filters 211, 212, 213, 214 instead of the single-stage filters 211, 212, 213, 214.

Following the CNN layer 527 is a postposition layer 529. The postposition layer 529 performs an operation on the bias data for a plurality of channels from the CNN layer 527 and outputs a medical image having no noise as an output of the machine learning model 521-5. The output medical image is a medical image corresponding to the medical image #1, such as an image obtained by removing noise from the medical image #1. The postposition layer 529 has at least one or more fully connecting layers and an output layer, but in addition to these layers, it may have any layer such as one or more CNN layers, a pooling layer, and a normalization layer.

It should be noted that in the case of a machine learning model having a plurality of CNN layers, numerical data need not necessarily be input to each CNN layer.

FIG. 17 is a drawing schematically showing input and output of a machine learning model 521-6 having a plurality of CNN layers 531. The machine learning model 521-6 shown in FIG. 17 has, as an example, a series of three layers; a CNN layer 531-1, a CNN layer 531-2 and a CNN layer 531-3. The postposition layer 533 is provided after the CNN 531-3. The CNN 531-1 receives an input medical image, the CNN layer 531-2 receives output data from the CNN layer 531-1, and the CNN layer 531-3 receives output data from the CNN layer 531-2. The postposition layer 533 receives the output data from the CNN layer 531-3, and outputs, for example, a medical image in which noise is removed from the input medical image #1 as an output of the machine learning model 521-6. The network structures of the CNN layer 531-1, the CNN layer 531-2 and the CNN layer 531-3 may be identical or different, and may be designed arbitrarily.

As shown in FIG. 17, numerical data #2 may not be input for all three layers; the CNN layer 531-1, the CNN layer 531-2 and the CNN layer 531-3. For example, the numerical data #2 may be input not to the CNN layer 531-1 closest to the input side, but only to subsequent layers; the CNN layer 531-2 and the CNN layer 531-3. Not limited thereto, the numerical data #2 may be input only to CNN layer 531-1 closest to the input side, but not to the subsequent layers; CNN layer 531-2 and CNN layer 531-3. Alternatively, the numerical data #2 may be input to any one CNN layer among the CNN layer 531-1, the CNN layer 531-2, and the CNN layer 531-3, but not to other CNN layers. Of course, the numerical data #2 may be input to all of the CNN layer 531-1, the CNN layer 531-2, and the CNN layer 531-3.

In the above embodiment, the output of the machine learning model is assumed to output a medical image having no noise. However, the output of the machine learning model, is not limited thereto.

For example, the machine learning model may output a segmentation result of the medical image from the medical image and the numerical data. For example, in response to the input of a T1-weighted image or a T2-weighted image, an image in which an anatomical tissue or a lesion area is divided is output as a segmentation result. The lesion area is, for example, an image area suspected of having cerebral infarction, ischemia, or cancer. The identification result of the medical image may be output from the medical image and the numerical data. For example, for the input of a T1-weighted image, a T2-weighted image, or a combination of a T1-weighted image and a T2-weighted image, the probability of being a cerebral infarction is output as an identification result. The segmentation result of the medical image may be output from the medical image and the numerical data. For example, in response to the input of the T1-weighted image, the T2-weighted image, or the combination of the T1-weighted image and the T2-weighted image, an image in which an image region having likelihood of cerebral infarction is segmented is output as a segmentation result.

Even when training is performed based on medical images of different image types such as the T1-weighted images and the T2-weighted images, some of the parameters of the machine learning model are shared. Thus, the machine learning model can acquire versatility for inputting medical images of different image types while suppressing lowering of reduction in learning efficiency.

The machine learning model may output super resolution data of the medical data from the medical data and the numerical data. Super resolution data is medical data having a higher spatial resolution than input medical data. It is possible to generate the machine learning model by making DNN learned based on input data including medical data and numerical data and super resolution data that is teacher data.

For example, when k-space data is acquired by a frequency-limited half-Fourier method, the k-space data is partially lost and the spatial resolution is lowered. My making DNN based on input data including k-space data and numerical data acquired by the half Fourier method and k-space data (teacher data) acquired from MR imaging without frequency limitation, the machine learning model can be generated. By using the machine learning model, it is possible to output k-space data (super resolution data) in which a data deficient part is restored from k-space data acquired by the half Fourier method.

The machine learning model shown above can be generated by the model learning apparatus 6 using supervised machine learning. The training sample is prepared by acquiring medical data under various acquisition conditions. Specifically, the input data of the training sample includes input medical data acquired under a certain acquisition condition, and numerical data obtained by digitizing the acquisition condition. The output data of the training sample includes output medical data corresponding to the medical data and according to the purpose of the machine learning model. The output data is, for example, medical data in which noise is reduced as compared to input medical data if the purpose of the machine learning model is de-noising.

In the training function 612, the processing circuitry 61 applies input medical data and numerical data to a machine learning model to perform forward propagation processing, and outputs output medical data. Next, the processing circuitry 61 applies the difference (error) between an estimated output medical data and the correct output medical data to the machine learning model to perform back propagation processing, and calculates a gradient vector. Next, the processing circuitry 61 updates parameters such as a weighting matrix and a bias of the machine learning model based on the gradient vector. By repeating the forward propagation processing, the back propagation processing, and parameter updating processing while changing the training sample, a learned machine learning model is generated.

As described above, the medical information processing apparatus 50 includes the processing circuitry 51. The processing circuitry 51 acquires medical data on a subject, acquires numerical data obtained by digitizing an acquisition condition of the medical data, and applies a machine learning model 521 to input data including the numerical data and the medical data, thereby generating output data based on the medical data.

According to the above configuration, the machine learning model 521 uses, in addition to the medical data, numerical data obtained by digitizing the acquisition condition corresponding to the medical data, and therefore, compared to the case where only the medical data is input, the accuracy of output data can be improved. The number of the elements of the numerical data corresponds to the number of predetermined candidate conditions, and the value of each element is a value according to whether or not the candidate condition in question is adopted. In other words, since the rules for digitizing the acquisition conditions are predetermined, it is possible for the machine learning model to accurately determine the acquisition conditions at the time of learning or application. This is also one factor to improve the accuracy of the output data.

According to at least one embodiment described above, the accuracy of output data using machine learning can be improved.

The term "processor" used in the above description is intended to mean, for example, CPU, GPU, or circuits such as an application specific integrated circuit (ASIC), a programmable logic apparatus (for example, a simple programmable logic device (SPLD) a complex Programmable Logic devices (CPLD), and a field programmable gate arrays (FPGA). The processor implements the respective functions 511 to 516 by reading and executing the program stored in the memory circuit. It should be noted that the program may be directly incorporated in the circuit of the processor instead of storing the program in the memory circuit. In this case, the processor implements the respective functions 511 to 516 by reading and executing a program incorporated in the circuit. Further, instead of executing a program, each function 511 to 516 corresponding to the program may be realized by a combination of logic circuits. It should be noted that each processor according to the present embodiment is not limited to being configured as a single circuit for each processor, and may be configured as one processor by combining a plurality of independent circuits to realize the function. Furthermore, the plurality of components in FIGS. 1, 3 and 7 may be integrated into one processor to realize its function.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical information processing apparatus comprising a processing circuitry,
the processing circuitry being configured to
acquire numerical data obtained by digitizing an acquisition condition of medical data of the subject, wherein the acquisition condition includes at least one of a type of pulse sequence, a frame number, a type of k-space filling trajectory, a number of times of repetition of repetition operation or an acceleration factor of parallel imaging,
acquire, as the medical data, raw data acquired by medical imaging according to the acquisition condition,
apply a machine learning model to input data including (1) the numerical data and (2a) the medical data or (2b) a medical image based on the medical data to generate output data based on the medical data or the medical image, and
output as the output data at least one of de-noised medical data, segmented image data, or super resolution data.

2. The medical information processing apparatus according to claim 1, wherein the machine learning model receives inputs of the numerical data and the medical data and learns using teacher data.

3. The medical information processing apparatus according to claim 1, wherein
the numerical data includes an element having two or more finite number of elements,
the number of the elements corresponds to a number of a plurality of candidate conditions corresponding to the acquisition condition, and
the value of the element corresponds to a numerical value according to whether or not the acquisition condition is adopted for the candidate conditions and/or a value.

4. The medical information processing apparatus according to claim 3, wherein the value of the element has one of a first value indicating that the acquisition condition is adopted and a second value indicating that the acquisition condition is not adopted.

5. The medical information processing apparatus according to claim 3, wherein
the numerical data includes an element having two or more finite number of elements, and
the elements by the number of the elements include a first element corresponding to the candidate conditions and a second element corresponding to none of the candidates.

6. The medical information processing apparatus according to claim 1, wherein the processing circuitry generates data to be provided for medical diagnosis on the subject as the output data.

7. The medical information processing apparatus according to claim 1, wherein the machine learning model is configured to multiply each of the numerical data and the medical data by weight different and add a product for each channel.

8. The medical information processing apparatus according to claim 1, wherein the processing circuit performs reconstruction processing on the input data including the numerical data and the raw data using the machine learning model to generate the image data on the subject.

9. The medical information processing apparatus according to claim 1, wherein
the acquisition condition is a number of times of acquisition and/or a direction of acquisition for each data acquisition trajectory, and
the numerical data is mask data in which a numerical value corresponding to the number of times of acquisition and/or the direction of acquisition in target imaging is assigned to a plurality of data acquisition trajectory candidates having a finite number of elements.

10. The medical information processing apparatus according to claim 9, wherein the processing circuitry determines the number of times of acquisition and/or the direction of acquisition for the data acquisition trajectory candidates according to a user's instruction or automatically.

11. The medical information processing apparatus according to claim 9, wherein the processing circuitry determines the number of times of acquisition and/or the direction of acquisition for the data acquisition trajectory candidates according to a predetermined rule based on an imaging time in the medical imaging.

12. The medical information processing apparatus according to claim 9, wherein the numerical value includes a first numerical value indicating that data acquisition is to be performed and a second numerical value indicating that data acquisition is not to be performed.

13. The medical information processing apparatus according to claim 9, wherein each of the data acquisition trajectory candidates is a data acquisition trajectory in k-space related to a radial method, and linearly passes substantially a center of the k-space.

14. The medical information processing apparatus according to claim 13, wherein an angular interval between the data acquisition trajectory candidates is set to a predetermined angle.

15. The medical information processing apparatus according to claim 13, wherein the data acquisition trajectory candidates are arranged at substantially equal intervals at an angle based on an angle obtained by dividing 360 degrees by the number of the elements.

16. The medical information processing apparatus according to claim 9, wherein each of the data acquisition trajectory candidates is a data acquisition trajectory in k-space related to a spiral method, and spirally passes through the k-space.

17. The medical information processing apparatus according to claim 9, wherein the processing circuitry applies the machine learning model to the mask data and the raw data, generates de-noised raw data as the output data, and performs Fourier transformation on the de-noised raw data to generate the medical image.

18. The medical information processing apparatus according to claim 9, wherein the processing circuitry performs Fourier transformation on the raw data to generate a provisional medical image, and applies the machine learning model to the mask data and the provisional medical image.

19. The medical information processing apparatus according to claim 1, further comprising an imaging apparatus configured to perform magnetic resonance imaging on the subject and acquire k-space data as the medical data.

20. A medical information processing method comprising:
acquiring numerical data obtained by digitizing an acquisition condition medical data of the subject, wherein the acquisition condition includes at least one of a type of pulse sequence, a frame number, a type of k-space filling trajectory, a number of times of repetition of repetition operation or an acceleration factor of parallel imaging;
acquiring, as the medical data, raw data acquired by medical imaging according to the acquisition condition,
applying a machine learning model to input data including (1) the numerical data and (2a) the medical data or (2b) a medical image based on the medical data to generate output data based on the medical data or the medical image; and
outputting as the output data at least one of de-noised medical data, segmented image data, or super resolution data.

* * * * *